(12) United States Patent
Yerramilli et al.

(10) Patent No.: US 6,365,352 B1
(45) Date of Patent: Apr. 2, 2002

(54) PROCESS TO STUDY CHANGES IN GENE EXPRESSION IN GRANULOCYTIC CELLS

(75) Inventors: Subrahmanyam V. Yerramilli, Montgomery Village, MD (US); Yatindra Prashar, Monmouth Junction, NJ (US); Peter Newburger, Waban; Jon Goguen, Holden, both of MA (US); Sherman M. Weissman, Hew Haven, CT (US)

(73) Assignees: Yale University, New Haven, CT (US); Gene Logic, INC, Gaithersburg, MD (US); University of Massachuetts, Worcester, MA (US)

( * ) Notice: Subject to any disclaimer, the term of this patent is extended or adjusted under 35 U.S.C. 154(b) by 0 days.

(21) Appl. No.: 09/506,729

(22) Filed: Feb. 18, 2000

Related U.S. Application Data

(63) Continuation of application No. PCT/US98/17284, filed on Aug. 21, 1998.
(60) Provisional application No. 60/056,844, filed on Aug. 22, 1997.

(51) Int. Cl.[7] .................................................. C12Q 1/68
(52) U.S. Cl. ......................................................... 435/6
(58) Field of Search ............................. 435/6, 4, 7.24; 536/23.1

(56) References Cited

U.S. PATENT DOCUMENTS 5,721,351 A * 2/1998 Levinson

FOREIGN PATENT DOCUMENTS

WO    WO 97/05286    2/1997

OTHER PUBLICATIONS

Roberge et al (1996) J. Immunology 156:4884–4891.*

Tam et al (1994) Am. J. Pathol. 145:126–136.*

Tam et al., 1996. "Differential Expression of Macrophage Inflammatory Protein–2 and Monocyte Chemoattractant Protein–1 in Experimental Glomerulonephritis", *Kidney International*. 49:715–721.

Prashar et al., 1996. "Analysis of Differential Gene Expression by Display of 3' End Restriction Fragments of cDNAs". Proc. Natl. Acad. Sci. USA. 93:659–663.

* cited by examiner

Primary Examiner—Robert A. Schwartzman
Assistant Examiner—Bronwen M. Loeb
(74) Attorney, Agent, or Firm—Morgan, Lewis & Bockius LLP

(57) ABSTRACT

The present invention comprises a method to identify granulocytic cell genes that are differentially expressed upon exposure to a pathogen or in a sterile inflammatory disease by preparing a gene expression profile of a granulocytic cell population exposed to a pathogen or isolated from a subject having a sterile inflammatory disease and comparing that profile to a profile prepared from quiescent granulocytic cells. The present invention is particularly useful for identifying cytokine genes, genes encoding cell surface receptors and genes encoding intermediary signaling molecules. The invention also includes methods to identify a therapeutic agent that modulates the expression of at least one gene in a granulocytic population. Genes which are differentially expressed during neutrophil contact with a pathogen, such as a virulent bacteria, or that are differentially expressed in a subject having a sterile inflammatory disease are of particular importance.

24 Claims, 11 Drawing Sheets

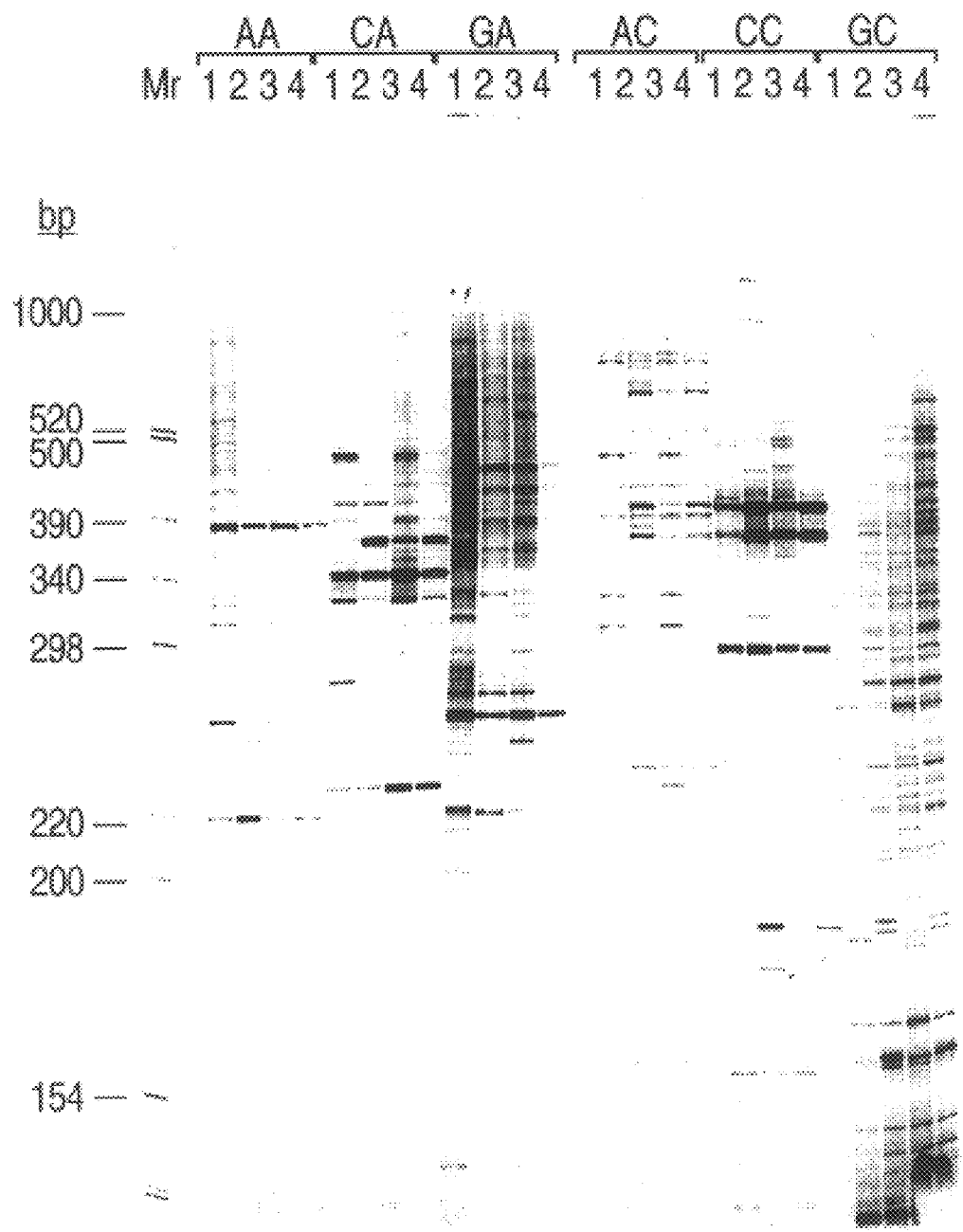

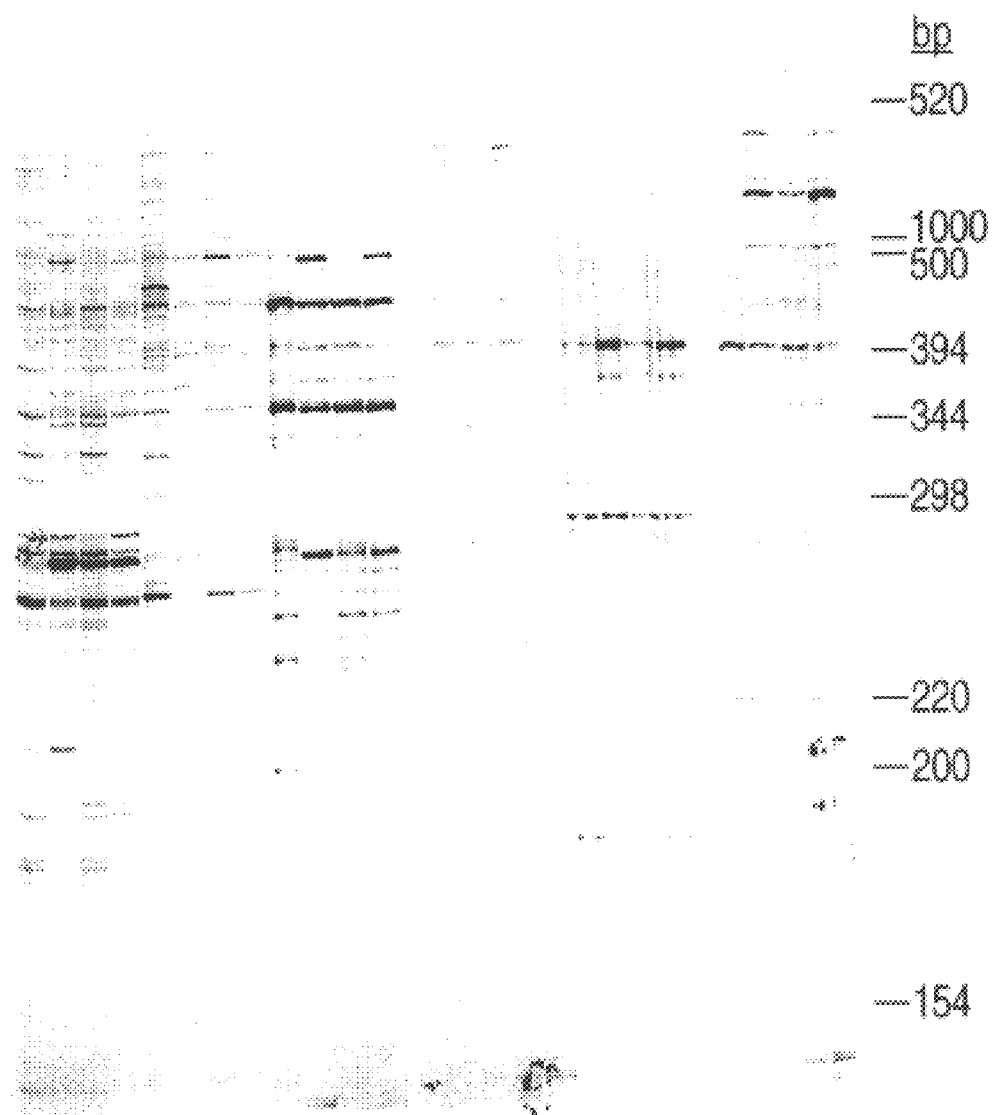

FIG. 4A

Differential Display Summary of Results (I) Known Genes

| No. | Clones | N1N2 | Expression Patterns | | | | Gene Bank Search and Analysis |
|---|---|---|---|---|---|---|---|
| | | | Control | E. coli | Virulent | Avirulent | |
| 1 | NP102-3 | AA | 0 | + | 0 | + | NADH-ubiquinone oxidoreductase ASHI subunit |
| 2 | IN12-B12 | AC | + | +++ | ++ | ++++ | human ubiquitin/polyubiquitin |
| 3 | NP104-5 | AA | + | +++ | ++ | ++ | MAP kinase kinase 3b |
| 4 | NP131-3 | CA | ++ | + | +++ | ++++ | cdc2/CDC28-like protein kinase (clk1) |
| 5 | B20-4 | AC | +++ | ++ | ± | + | human cyclin-dependent kinase inhibitor |
| 6 | NP119-1 | AG | 0 | + | 0 | ++ | bcl-2 related (bfl-1) mRNA |
| 7 | NP126-3 | AT | 0 | +++ | + | +++ | human B-cell lymphoma 3-encoded protein bcl-3 mRNA |
| 8 | NP124-3 | AT | ++ | +++ | ++ | +++ | helix-loop-helix basic phosphoprotein (GOS8) |
| 9 | B14-3 | AC | ++ | +++ | 0 | + | human nucleolar phosphoprotein B23 (nucleophosmin) |
| 10 | IN23-E11 | AC | ± | +++ | + | +++ | LD78 β (human homolog of mouse MIP1α) |
| 11 | NP125-2 | AT | 0 | ++ | ± | ++ | LD78 receptor (HM74) |
| 12 | NP149-1 | CG | +++ | + | ++ | ++ | vacuolar H+ pumping ATPase (16KD proteolipid subunit) |
| 13 | B23-2 | AC | ++ | +++ | + | ++ | vacuolar H+ pumping ATPase (56KD subunit) |
| 14 | NP139-1 | CC | ± | ++ | + | +++ | plasma membrane Ca2+ pumping ATPase (56KD subunit) |

FIG. 4B

Differential Display Summary of Results (I) Known Genes

| No. | Clones | N1N2 | Expression Patterns | | | | Gene Bank Search and Analysis |
|---|---|---|---|---|---|---|---|
| | | | Control | E. coli | Virulent | Avirulent | |
| 15 | NP105-1 | AA | ++++ | ± | + | ++ | human H3.3 gene exon 4 |
| 16 | NP128-3 | CA | 0 | + | ++ | ++++ | ribosomal protein S19 |
| 17 | IN20-E8 | AC | + | ± | ++ | ± | ribosomal protein S20 |
| 18 | NP127-2 | AT | + | + | ± | + | poly(A) binding protein II |
| 19 | NP103-3 | AA | ++ | +++ | + | ++++ | Spermidine/Spermine N1-acetyltransferase |
| 20 | NP132-2 | CA | + | ±0 | + | ++ | human GDP-dissociation inhibitor (LY-GD1) |
| 21 | B4-1 | AC | +++ | +++ | + | + | bovine GTP binding regulatory protein γ-6 subunit |
| 22 | NP107-2 | AA | ++++ | ++ | +++ | +++ | human B4-2 protein |
| 23 | NP156-1 | CG | ++ | + | ++ | ++ | ras-related protein p23/Rab-7 |
| 24 | B5-4 | AC | ± | +++ | + | ++ | mouse ras-related YTP1 protein/Rab-1A |
| 25 | B14-4 | AC | + | +++ | + | ++++ | human pre-B cell enhancing factor (PBEF) |
| 26 | B22-2 | AC | ++ | +++ | + | ++ | human complement decay accelerating factor |
| 27 | Bam1 | AC | + | ++ | +++ | ++ | TNFα inducible protein B94 |

FIG. 4C

Differential Display Summary of Results (I) EST Sequences

| No. | Clones | N1N2 | Expression Patterns | | | | Gene Bank Search and Analysis |
|-----|--------|------|---------|--------|---------|----------|-------------------------------|
|     |        |      | Control | E. coli | Virulent | Avirulent |                               |
| 1   | NP101-3 | AA  | ++      | ++     | 0       | ++       | EST (GB/L81699/HSL81699)      |
| 2   | NP108-3 | AA  | ++      | +      | +       | ++       | EST (GB/R09487/R09487)        |
| 3   | NP113-2 | AG  | ++      | +      | ++      | +        | EST (GB/U79267/HSU79267)      |
| 4   | NP114-2 | AG  | +++     | +      | ++      | +++      | EST (GB/N26756/N26756)        |
| 5   | NP115-3 | AG  | ++      | +      | +++     | +++      | EST (GB/L49761/HUM78188)      |
| 6   | NP116-3 | AG  | +       | +      | ++      | +        | EST (EMB/F10736/HSC3IC022)    |
| 7   | NP117-2 | AG  | ±       | ++++   | ++      | ++++     | EST (GB/AA004905/AA004905)    |
| 8   | NP120-3 | AG  | ±       | +      | ++      | +        | EST (GB/R16810/R16810)        |
| 9   | NP121-2 | AG  | ±       | ++     | +       | ++       | EST (GB/AA159075/AA159075)    |
| 10  | NP122-1 | AT  | 0       | +      | ±       | ++       | EST (GB/AA016979/AA016979)    |
| 11  | NP133-1 | CA  | +++     | ++     | +++     | +++      | EST (GB/AA190718/AA190718)    |
| 12  | NP134-2 | CA  | 0       | ±      | ++      | +        | EST (GB/T29287/T29287)        |
| 13  | NP138-1 | CC  | +       | ++     | +       | +++      | EST (GB/T58520/T58520)        |
| 14  | NP150-1 | CG  | +       | +++    | +++     | ++++     | EST (GB/AC001223/HSAC001223)  |
| 15  | B7-1   | AC  | ++      | +      | +       | 0        | EST (DJB/D60083/HUM0084H05A)  |

FIG. 4D

Differential Display   Summary of Results (I)   EST Sequences

| No. | Clones | N1N2 | Expression Patterns | | | | Gene Bank Search and Analysis |
|---|---|---|---|---|---|---|---|
| | | | Control | E. coli | Virulent | Avirulent | |
| 16 | B8-1 | AC | +++ | + | ++ | 0 | EST (GB/R37008/R37008) |
| 17 | B10-1 | AC | +++ | ++ | 0 | + | EST (GB/W67981/W67981) |
| 18 | B12-2 | AC | ++ | +++ | + | + | EST (GB/N24729/N24729) |
| 19 | B13-4 | AC | +++ | ++ | + | + | EST (GB/N23012/N23012) |
| 20 | B15-2 | AC | +++ | ± | ++ | ± | EST (GB/R49664/R49664) |
| 21 | B17-2 | AC | ++++ | +++ | ++ | + | EST (GB/T34605/T34605) |
| 22 | B18-2 | AC | ++++ | ++ | +++ | ± | EST (GB/AA055573/AA055573) |
| 23 | B19-5 | AC | + | ++ | + | ++ | EST (GB/AA076421/AA076421) |
| 24 | B21-3 | AC | +++ | +++ | + | +++ | EST (GB/AA150905/AA150905) |
| 25 | IN10-B10 | AC | + | ++++ | + | + | EST (GB/N21073/N21073) |
| 26 | IN19-E7 | AC | 0 | +++ | 0 | ++ | EST (GB/AA044087/AA044087) |
| 27 | IN21-E9 | AC | + | ++ | + | ++ | EST (GB/H44997/H44997 |
| 28 | IN22-E10 | AC | ++++ | ++ | +++ | + | EST (GB/N50114/N50114) |
| 29 | Bcl | AC | +++ | +++ | + | ++ | EST (EMB/Z39133/HSC11B122 |

FIG. 6

|  | 1 | 2 | 3 | 4 | $N_1 N_2$ | ENZYME |
|---|---|---|---|---|---|---|
| MIP1α | ■ | ■ | ░ | ▬ | AC | Eco RI |
| LD78 Receptor |  |  |  | ▬ | AT | Bgl II |

1. Neutrophils alone
2. Neutrophils + *E.coli*
3. Neutrophils + Virulent *y. pestis*
3. Neutrophils + Avirulent *y. pestis*

SEQUENCE LISTING

```
<160> NUMBER OF SEQ ID NOS: 66

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:  Primer

<400> SEQUENCE: 1
ctctcaagga tctaccgct                                                19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 2
cagggtagac gacgctacgc                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 3
taataccgcg ccacatagca                                               20

<210> SEQ ID NO 4
<211> LENGTH: 55
<212> TYPE: DNA
<213> ORGANISM: Artificial Sequence
<220> FEATURE:
<223> OTHER INFORMATION: Description of Artificial Sequence:  Primer
<220> FEATURE:
<221> NAME/KEY: variation
<222> LOCATION: (55)
<223> OTHER INFORMATION: v = a or c or g.

<400> SEQUENCE: 4
acgtaatacg actcactata gggcgaattg ggtcgacttt tttttttttt ttttv        55

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence:  Primer

<400> SEQUENCE: 5
```

```
ctctcaagga tcttaccgct tttttttttt tttttttat                              40
```

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 6

```
taataccgcg ccacatagca tttttttttt ttttttttcg                             40
```

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 7

```
cagggtagac gacgctacgc tttttttttt tttttttga                              40
```

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Adapter

<400> SEQUENCE: 8

```
tagcgtccgg cgcagcgacg gccag                                             25
```

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Adapter

<400> SEQUENCE: 9

```
gatcctggcc gtcggctgtc tgtcggcgc                                         29
```

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: variation
<222> LOCATION: (39)..(40)
<223> OTHER INFORMATION: v at position 39 = a or c or g;
      n at position 40 = a or c or g or t.

<400> SEQUENCE: 10

```
tgaagccgag acgtcggtcg tttttttttt ttttttttvn                             40
```

<210> SEQ ID NO 11
<211> LENGTH: 52
<212> TYPE: DNA
<213> ORGANISM: Homo sapiens

<400> SEQUENCE: 11

```
tctcagtgag ctgagatcac accactgcac tccaactggg cgacagagca ag               52
```

<210> SEQ ID NO 12
<211> LENGTH: 51
<212> TYPE: DNA
<213> ORGANISM: Homo sapiens

<400> SEQUENCE: 12

```
cactttcccc aaattctttt gccatagttc actctctact gataaggcca c          51
```

<210> SEQ ID NO 13
<211> LENGTH: 111
<212> TYPE: DNA
<213> ORGANISM: Homo sapiens

<400> SEQUENCE: 13

```
gggaaagtgg tggggtggtg agggtcaatg tgcagaaaat cgatgtaact tgtaatacag   60
ttgagtcaac tgtgtgttca caacaactct gagagttaac accatttcta c          111
```

<210> SEQ ID NO 14
<211> LENGTH: 166
<212> TYPE: DNA
<213> ORGANISM: Homo sapiens

<400> SEQUENCE: 14

```
atctaaatat ttttcatacc gagttattaa ggagtcagta gtctgtgcta caatgctgca   60
aaaagcatca cgtggaagaa tgggaactat gcgtacttta tgaagtgatg tataacacaa  120
tgaactctgt tttacaacta cagtgctgca ttcaattatc ttccat                166
```

<210> SEQ ID NO 15
<211> LENGTH: 271
<212> TYPE: DNA
<213> ORGANISM: Homo sapiens

<400> SEQUENCE: 15

```
aagctctgta tacaaaagtt atttatttag atgttcgagg catgtctctc ctcacctgta   60
aactaactgt tttataacag cttgtatcac atgtgtgaag ttaatgaatg taatactcca  120
acaagccatt catcagattg gccaacagct aggatacagt taaataatgg cgaccaggtt  180
gacaagtcat aattgcggtt tgggggaccg tagttgcacc tcacctagac caacgtacgc  240
atggcactcg acccaggcga acaaaattaa t                                271
```

<210> SEQ ID NO 16
<211> LENGTH: 350
<212> TYPE: DNA
<213> ORGANISM: Homo sapiens

<400> SEQUENCE: 16

```
tttctcaaga agagataaga atgaaaagtc atagaacaca tcatggagga cctggacaca   60
aatgcagaca agcagctgag cttcgaggag ttcatcatgc tgatggcgag gctaacctgg  120
gcctcccacg agaagatgca cgagggtgac gatggccctg ccaccacca taagccaggc  180 ctcggggagg gcaccccta agaccacagt ggacaagatc acagtggcca cggacacggc  240
cacagtcatg gtggccacgg ccacagccac taatcaggag gccaggccac cctgcctcta  300
cccaaccagg gccccggggc ctgttatgtc aaactgtctt ggctgtgggg             350
```

<210> SEQ ID NO 17
<211> LENGTH: 455
<212> TYPE: DNA
<213> ORGANISM: Homo sapiens
<220> FEATURE:

-continued

```
<221> NAME/KEY: unsure
<222> LOCATION: (1)..(29)
<223> OTHER INFORMATION: n = a or c or g or t.

<400> SEQUENCE: 17
ngatctttct aggagggaga cactggccnc tcaaatcgtc cagcgacctt cctcatccac      60
cccatccctc cccagttcat tgcactttga ttagcagcgg aacaaggagt cagacatttt    120
aagatggtgg cagtagaggc tatggacagg gcatgccacg tgggctcata tggggctggg    180
agtagttgtc tttcctggca ctaacgttga gccctggag gcactgaagt gcttagtgta     240
cttggagtat tggggtctga ccccaaacac cttccagctc ctgtaacata ctggcctgga    300
ctgtttctc tcggctcccc atgtgtcctg gttcccgttt ctccacctag actgtgaacc     360
tctcgagggc aggaccaca ccctgtactg ttctgtgtct ttcacagctc ctcccacaat     420
gctgaatata cagcaggtgc tcaataaatg attct                               455

<210> SEQ ID NO 18
<211> LENGTH: 35
<212> TYPE: DNA
<213> ORGANISM: Homo sapiens

<400> SEQUENCE: 18
gcaagtgtgt tgtgttacag tgtcacaaca ccgag                                35

<210> SEQ ID NO 19
<211> LENGTH: 71
<212> TYPE: DNA
<213> ORGANISM: Homo sapiens

<400> SEQUENCE: 19
gatctctccc tacgcaaaac gtattgtagt gaaagggtct tctttactac cttaataaaa     60
cagctagtgt g                                                          71

<210> SEQ ID NO 20
<211> LENGTH: 78
<212> TYPE: DNA
<213> ORGANISM: Homo sapiens

<400> SEQUENCE: 20
gatctaaata caaaggatat acagtcttga atctaaaata atttgctaac tattttgatt     60
cttcagagag aactacta                                                   78

<210> SEQ ID NO 21
<211> LENGTH: 98
<212> TYPE: DNA
<213> ORGANISM: Homo sapiens

<400> SEQUENCE: 21
gatctagtcc ggacatgctg tgtatattgt aacgttaaat gaaaaagaa ccccccttttg     60
tattatagtc atgcggtctt atgtatgata aacagttg                             98

<210> SEQ ID NO 22
<211> LENGTH: 114
<212> TYPE: DNA
<213> ORGANISM: Homo sapiens

<400> SEQUENCE: 22
gatcttttgt agtcacctct gtatcttatg tctggttgag gggtgctttt acttgtctgg     60
catttgcatt caatgatctt tcagtcatgt cagttagact aaaaattatt tctg          114
```

<210> SEQ ID NO 23
<211> LENGTH: 122
<212> TYPE: DNA
<213> ORGANISM: Homo sapiens

<400> SEQUENCE: 23

```
cccaagcccc ttggacactg cagctctttt cagttttttgc ttacacacaa ttcattcttt      60
gcagctaatt aagccgaaga agcgtgggaa tcaagtttgg aacagagatt aaaaaagttc     120
tt                                                                    122
```

<210> SEQ ID NO 24
<211> LENGTH: 123
<212> TYPE: DNA
<213> ORGANISM: Homo sapiens

<400> SEQUENCE: 24

```
gctctggagg acaatccagg aactacatta cctggactgt atgctggtca tttctacaga      60
cagcattcag tatttgagtg tacggtaact gtctggggtg attcctataa gatcattata     120
ctg                                                                   123
```

<210> SEQ ID NO 25
<211> LENGTH: 151
<212> TYPE: DNA
<213> ORGANISM: Homo sapiens

<400> SEQUENCE: 25

```
gatctttctc cttgaatatc tttcgataaa caacaaggtg gtgtgatctt aatatatttg      60
aaaaaaactt cattctcgtg agtcatttaa atgtgtacaa tgtacacact ggtacttaga     120
gtttctgttt gattcttttt taataaacta c                                    151
```

<210> SEQ ID NO 26
<211> LENGTH: 92
<212> TYPE: DNA
<213> ORGANISM: Homo sapiens

<400> SEQUENCE: 26

```
tgtcactcat gccctgggac tgcttctcca gccaggcggg cgccatacgt cccacactag      60
tgaaggtcaa tgtctcagaa caacacctct at                                    92
```

<210> SEQ ID NO 27
<211> LENGTH: 162
<212> TYPE: DNA
<213> ORGANISM: Homo sapiens

<400> SEQUENCE: 27

```
gatctggcct gttcctgcgt ctgcggagca ggccttgtct cccagctatc tataacctta      60
cctagagtgt cgacttgtgg gttcctgttg ctgagacttc ctggatggag ccgccctcac     120
cgccggaccc gtagcactgc gcggaactgt gtccaataaa gt                        162
```

<210> SEQ ID NO 28
<211> LENGTH: 166
<212> TYPE: DNA
<213> ORGANISM: Homo sapiens

<400> SEQUENCE: 28

```
gatctgattt gctagttctt ccttgtagag ttataaatgg aaagattaca ctatctgatt      60
```

-continued

| aatagtttct tcatactctg catataattt gtggctgcag aatattgtaa tttgttgcac | 120 |
| actatgtaac aaaacaactg aagatatgtt taataaatat tgtact | 166 |

<210> SEQ ID NO 29
<211> LENGTH: 274
<212> TYPE: DNA
<213> ORGANISM: Homo sapiens

<400> SEQUENCE: 29

| gatctttatg agagcagtat tttctgtgtt ttcttttttaa tttacagcct ttcttatttt | 60 |
| gatattttt taatgttgtg gatgaatgcc agctttcaga cagagcccac ttagcttgtc | 120 |
| cacatggatc tcaatgccaa tcctccattc ttcctctcca gatattttg ggagtgacaa | 180 |
| acattctctc atcctactta gcctacctag atttctcatg acgagttaat gcatgtccgt | 240 |
| ggttgggtgc acctgtagtt ctgtttattg gtca | 274 |

<210> SEQ ID NO 30
<211> LENGTH: 279
<212> TYPE: DNA
<213> ORGANISM: Homo sapiens

<400> SEQUENCE: 30

| gatctaagtt agtccaaaag ctaaatgatt taaagtcaag ttgtaatgct aggcataagc | 60 |
| actctataat acattaaatt ataggccgag caattaggga atgtttctga aacattaaac | 120 |
| ttgtatttat gtcactaaaa ttctaacaca aacttaaaaa atgtgtctca tacatatgct | 180 |
| gtactaggct tcatcatgca tttctaaatt tgtgtatgat ttgaatatat gaaagaattt | 240 |
| atacacgagt gttatttaaa attattaaaa ataaatgta | 279 |

<210> SEQ ID NO 31
<211> LENGTH: 289
<212> TYPE: DNA
<213> ORGANISM: Homo sapiens

<400> SEQUENCE: 31

| gatcttatag gcctgtctca tcaggttggt gtcagcccag ctaggattag gcagaattgg | 60 |
| gtggggctg tagtgcactt ttggcacagc atgtacctgt ctgactaatt ctctgtcttt | 120 |
| tctttcctgt tgcaattcat gggtcttagc atcttctgaa tggtgtttag taggtcatcc | 180 |
| tgttgatttc ctgctaggga gtagcatact ctggctctgt accactggcc aagggactta | 240 |
| aggatagatg aagggctgca gttttgttaa atggaacaat atgaagaga | 289 |

<210> SEQ ID NO 32
<211> LENGTH: 151
<212> TYPE: DNA
<213> ORGANISM: Homo sapiens

<400> SEQUENCE: 32

| gatctttctc cttgagtatc tttcgataaa caacaaagtg gtgtgatctt aatatatttg | 60 |
| aaaaaaactt cattctcgtg agtcatttaa atgtgtacaa tgtacacact ggtacttaga | 120 |
| gtttctgttt gattcttttt taataaacta c | 151 |

<210> SEQ ID NO 33
<211> LENGTH: 85
<212> TYPE: DNA
<213> ORGANISM: Homo sapiens

<400> SEQUENCE: 33

```
gatctctgct catagaatgc atggggagcc ttccagctca ctctccctga ggactggctt    60
gacaggggct atgggtttgc tttgg                                          85
```

<210> SEQ ID NO 34
<211> LENGTH: 190
<212> TYPE: DNA
<213> ORGANISM: Homo sapiens

<400> SEQUENCE: 34

```
gatctgcgct tccagagcgc agctatcggt gctttgcagg aggcaagtga ggcctatctg    60
gttggccttt ttgaagacac caacctgtgt gctatccatg ccaaacgtgt aacaattatg   120
ccaaaagaca tccagctagc acgccgcata cgtggagaac gtgcttaaga atccactatg   180
atgggaaaca                                                          190
```

<210> SEQ ID NO 35
<211> LENGTH: 242
<212> TYPE: DNA
<213> ORGANISM: Homo sapiens

<400> SEQUENCE: 35

```
gatctaaatg tgaacagttt actaatgcac tactgaagtt taaatctgtg gcacaatcaa    60
tgtaagcatg gggtttgttt ctctaaattg atttgtaatc tgaaattact gaacaactcc   120
tattcccatt tttgctaaac tcaatttctg gttttggtat atatccattc cagcttaatg   180
cctctaattt taatgccaac aaaattggtt gtaatcaaat tttaaaataa taataatttg   240
gc                                                                  242
```

<210> SEQ ID NO 36
<211> LENGTH: 216
<212> TYPE: DNA
<213> ORGANISM: Homo sapiens

<400> SEQUENCE: 36

```
gccttttcga tagtttcggg tcaggtaaaa atggcctcct ggcgtaagct tttcaaggtt    60
ttttggaggc tttttgtaaa ttgtgatagg aactttggac cttgaactta cgtatcatgt   120
ggagaagagc caatttaaca aactaggaag atgaaaaggg aaattgtggc caaaactttg   180
ggaaaaggag gttcttaaaa tcagtgtttc cccttt                             216
```

<210> SEQ ID NO 37
<211> LENGTH: 204
<212> TYPE: DNA
<213> ORGANISM: Homo sapiens

<400> SEQUENCE: 37

```
gatctatgca caagaacccc tttaccccat gaccaacatc gcagacacat gtgctggcca    60
cctgctgagc cccaagtgga acgagacaag cagcccttag cccttcccct ctgcagcttc   120
caggctggcg tgcagcatca gcatccctag aaagccatgt gcagccacca gtccattggg   180
caggcagatg ttcctaataa agct                                          204
```

<210> SEQ ID NO 38
<211> LENGTH: 304
<212> TYPE: DNA
<213> ORGANISM: Homo sapiens

<400> SEQUENCE: 38

```
gatctttcct cctggttact gtgaagcctg ttggtttgct gctgtcgttt ttgaggaggg    60
cccatggggg taggagcagt tgaacctggg aacaaacctc acttgagctg tgcctagaca   120
atgtgaattc ctgtgttgct aacagaagtg gcctgtaagc tcctgtgctc cggagggaag   180
catttcctgg taggctttga ttttctgtg tgttaaagaa attcaatcta ctcatgatgt    240
gttatgcata aaacatttct ggaacatgga tttgtgttca ccttaaatgt gaaaataaat   300
ccta                                                                304
```

<210> SEQ ID NO 39
<211> LENGTH: 312
<212> TYPE: DNA
<213> ORGANISM: Homo sapiens

<400> SEQUENCE: 39

```
atctttcctc ctggttactg tgaagcctgt tggtttgctg ctgtcgtttt tgaggagggc    60 ccatggggt aggagcagtt gaacctggga acaaacctca cttgagctgt gcctagacaa   120
tgtgaattcc tgtgttgcta acagaagtgg cctgtaagct cctgtgctcc ggagggaagc   180
atttcctggt aggctttgat tttctgtgt gttaaagaaa ttcaatctac tcatgatgtg    240
ttatgcataa aacatttctg gaacatggat ttgtgttcac cttaaatgtg aaaataaatc   300
ctattttcta tg                                                       312
```

<210> SEQ ID NO 40
<211> LENGTH: 355
<212> TYPE: DNA
<213> ORGANISM: Homo sapiens

<400> SEQUENCE: 40

```
gatctttggc agcgccattg gactctttgg ggtcatcgtc gcaattcttc atacctccag    60
agtgaagatg ggtgactaga tgatatgtgt gggtggggcc gtgcctcact tttatttatt   120
gctggttttc ctgggacagc tggagctgtg tcccttaacc tttcagaggc ttggtgttca   180
gggccctccc tgcactcccc tcttgctgcg tgttgatttg gaggcactgc agtccaggcc   240
gagtcctcag tgcggggagc aggctgctgc tgctgactct gtgcagctgc gcacctgtgt   300
cccccacctc caccctcaac ccatcttcct agtgtttgtg aaataaactt ggtat       355
```

<210> SEQ ID NO 41
<211> LENGTH: 255
<212> TYPE: DNA
<213> ORGANISM: Homo sapiens

<400> SEQUENCE: 41

```
gatcttccac gtctccatct cagtacacaa tcatttaata tttccctgtc ttaccctat     60 tcaagcaact agaggccaga aatgggcaa attatcacta acaggtcttt gactcaggtt   120
ccagtagttc attctaatgc ctagattctt ttgtggttgt tgctggccca atgagtccct   180
agtcacatcc cctgccagag ggagttcttc ttttgtgaga gacactgtaa acgacacaag   240
agaacaagaa taaaa                                                    255
```

<210> SEQ ID NO 42
<211> LENGTH: 299
<212> TYPE: DNA
<213> ORGANISM: Homo sapiens

<400> SEQUENCE: 42

```
ttatatattt ttcttaaata tgttttattg tcttctctaa gcaaaaagtt cttaataaac    60
```

```
atagtatttc tctctgcgtc ctatttcatt agtgaagaca tagttcacct aaaatggcat      120
cctgctctga atctagactt tttagaaatg gcatatgttt ttgatgatat gtcaacattc      180
aaaatagtcc taattaaatt gttggttaaa tgtaatgtca actctttata aacttaaata      240
taaacaagta attaaccact ctaagtaata aaacacattt cacctgtgtt ctgagtgta       299
```

<210> SEQ ID NO 43
<211> LENGTH: 518
<212> TYPE: DNA
<213> ORGANISM: Homo sapiens

<400> SEQUENCE: 43

```
atgaatcctt gccacctcca cctgcagaac tgttataaat attcaacctt gcttttttagc     60 tgatcttcca tcctcaaatg actcttttt ctttatatgt taacatatat aaaatggcaa      120
ctgatagtca attttgattt ttattcagga actatctgaa atctgctcag agcctatgtg     180
catagatgaa actttttttt aaaaaagtt atttaacagt aatctattta ctaattatag      240
tacctatctt taaagtatag tacattttac atatgtaaat ggtatgtttc ataattttaa    300
gaactctgaa acaatctaca tatacttatt acccagtaca gttttttttc ccctgaaaag     360
ctgtgtataa aattatggtg aataaacttt tatgttttcca tttcaaagac cagggtggag    420
aggaataaga gactaagtat atgcttcaag ttttaaatta ataccctcagg tattaaaata    480 aatattccaa gtttgtggga aatggggaga ttaaaatg                             518
```

<210> SEQ ID NO 44
<211> LENGTH: 332
<212> TYPE: DNA
<213> ORGANISM: Homo sapiens

<400> SEQUENCE: 44

```
ttatgtggcc ttaggtagct ggttgtacat ctttccctaa atcgatccat gttaccacat      60 agtagttttta gtttaggatt cagtaacagt gaagtgttta ctatgtgcaa cggtattgaa    120
gttcttatga ccacagatca tcagtactgt tgtctcatgt aatgctaaaa ctgaaatggt    180
ccgtgtttgc attgttaaaa atgatgtgtg aaatagaatg agtgctatgg tgttgaaaac    240
tgcagtgtcc gttatgagtg ccaaaaatct gtcttgaagg cagctacact ttgaagtggt    300 cttttgaatac ttttaataaa tttatttttga ta                                332
```

<210> SEQ ID NO 45
<211> LENGTH: 377
<212> TYPE: DNA
<213> ORGANISM: Homo sapiens

<400> SEQUENCE: 45

```
taggtgaacc cttattctgc agggttctcc ctcccacctt aaagaagttc cccttatgtg       60
ggttgcctgg tgaatggcct tccttcccgc cagagggctt gtgaacagac cggagaggac      120
agtggattgt ttatactcca gtgtacatag tgtaatgtag cgtgtttaca tgtgtagcct     180
atgttgtggt ccatcagccc ctcacattcc tagggggtttg agatgctgta cgtggtatgt    240
gacaccaaag ccacctctgt catttgttgt gatgtctttt cttggcaaaa gccttgtgta    300
tatttgtata ttacacattt gtacagaatt ttggaagatt ttcagtctag ttgccaaatc    360
tggctccttt acaaaag                                                   377
```

<210> SEQ ID NO 46

```
<211> LENGTH: 495
<212> TYPE: DNA
<213> ORGANISM: Homo sapiens

<400> SEQUENCE: 46
agaatctctt atgttctcag aggaaggtgg aagaaaccat gggcaggagt aggaattgag      60
tgataaacaa ttgggctaat gaagaaaact tctcttattg ttcagttcat ccagattata     120
acttcaatgg gacactttag accattagac aattgacact ggattaaaca aattcacata     180
atgccaaata cacaatgtat ttatagcaac gtataatttg caaagatgga ctttaaaaga    240
tgctgtgtaa ctaaactgaa ataattcaat tacttattat ttagaatgtt aaagcttatg    300
atagtctttt ctaattctta acactcatac ttgaaatctt tctgagtttc cccagaagag    360
aatatgggat ttttttttgac attttttgact catttaataa tgctcttgtg tttacctagt   420
atatgtagac tttgtcttat gtgtcaaaag tcctaggaaa gtggttgatg tttcttatag    480
caattaaaaa ttatt                                                      495

<210> SEQ ID NO 47
<211> LENGTH: 54
<212> TYPE: DNA
<213> ORGANISM: Homo sapiens

<400> SEQUENCE: 47
atctcagtga gctgagatca caccactgca ctccaactgg gcgacagagc aaga           54

<210> SEQ ID NO 48
<211> LENGTH: 92
<212> TYPE: DNA
<213> ORGANISM: Homo sapiens

<400> SEQUENCE: 48
gatctgtaat tcaggtgttt tctgtacagc catacgtaga taatgaagcc aaaaggcttt    60
taattacacc atggcctaaa ataaattcat ca                                   92

<210> SEQ ID NO 49
<211> LENGTH: 122
<212> TYPE: DNA
<213> ORGANISM: Homo sapiens

<400> SEQUENCE: 49 tattttttcag ctgagttatt agggagtcat tattctgtgg tacaatgctg caaaaagcat    60
catgtggaag aatgggaact atgcttacat tatgaagtga tgtataacac aatgcaaatc   120
tg                                                                    122

<210> SEQ ID NO 50
<211> LENGTH: 143
<212> TYPE: DNA
<213> ORGANISM: Homo sapiens

<400> SEQUENCE: 50
gatctttttt cattaaaaaa tgttcaatta tcaggccggg tgcagtgggg ctcatgcctg    60
taatcccaac actttgggag gccgatgcag gcggatcact aggtcagcag atcgagacca   120
tcctggctaa cacagtgaaa cct                                            143

<210> SEQ ID NO 51
<211> LENGTH: 211
<212> TYPE: DNA
<213> ORGANISM: Homo sapiens
```

-continued

<400> SEQUENCE: 51

| gatctttatt tttagccatg cactgttgtg aggaaaatta cctgtcttga ctgccatgtg | 60 |
| ttcatcatct taagtattgt aagctgctat gtatggattt aaaccgtaat catatctttt | 120 |
| tcctatctat ctgaggcact ggtggaataa agaacctgta tattttactt tgttgcagat | 180 |
| agtcttgccg catcttggca agttgcagag a | 211 |

<210> SEQ ID NO 52
<211> LENGTH: 284
<212> TYPE: DNA
<213> ORGANISM: Homo sapiens

<400> SEQUENCE: 52

| gatcttcgtg aagacctgac tggtaagacc atcaccctcg aggtggagcc cagtgacacc | 60 |
| atcgagaatg tcaaggcaaa gatccaagat aaggaaggca tccctcctga tcagcagagg | 120 |
| ttgatctttg ctgggaaaca gctggaagat ggacgcaccc tgtctgacta acatccag | 180 |
| aaagagtcca ctctgcactt ggtcctgcgc ttgaggggg gtgtctaagt ttccccttt | 240 |
| aaggtttcaa caaatttcat tgcactttcc tttcaataaa gttg | 284 |

<210> SEQ ID NO 53
<211> LENGTH: 300
<212> TYPE: DNA
<213> ORGANISM: Homo sapiens

<400> SEQUENCE: 53

| gatctttcct cctggttact gtgaagcctg ttggtttgct gctgtcgttt ttgaggaggg | 60 |
| cccatggggg taggagcagt tgaacctggg aacaaacctc acttgagctg tgcctagaca | 120 |
| atgtgaattc ctgtgttgct aacagaagtg gcctgtaagc tcctgtgctc cggagggaag | 180 |
| catttcctgg taggctttga tttttctgtg tgttaaagaa attcaatcta ctcatgatgt | 240 |
| gttatgcata aacatttct ggaacatgga tttgtgttca ccttaaatgt gaaataaat | 300 |

<210> SEQ ID NO 54
<211> LENGTH: 307
<212> TYPE: DNA
<213> ORGANISM: Homo sapiens

<400> SEQUENCE: 54

| gatctttcgg gttctctctc ctaactcagc tcttcgttcc cagaaaccca gatgtaatcc | 60 |
| ccctacgtgg tgcttggggc atcccgatac catctcagta aatctcctac attggcctcc | 120 |
| tcaccctccc cgggacccac accttcagg tcctcaccct gagacaggag ggaccctctg | 180 |
| agatcaggga cccttaggtc tcactgctct ctgattcata gctcaactgg gccccagtt | 240 |
| ccataccca gcattcccgg tcactccctc cctaatctga gcatcactca agctctttat | 300 |
| taaactc | 307 |

<210> SEQ ID NO 55
<211> LENGTH: 73
<212> TYPE: DNA
<213> ORGANISM: Homo sapiens

<400> SEQUENCE: 55

| atctctctcc ctacgcaaaa ccctattgta gtaaaaaagt cttctttact atcttaataa | 60 |
| aacagatatt gtg | 73 |

<210> SEQ ID NO 56
<211> LENGTH: 89
<212> TYPE: DNA
<213> ORGANISM: Homo sapiens

<400> SEQUENCE: 56
atctattctt gtagattttt tttgtgtggg tctatgtttc attcatctgc tttcaggctg     60
gatttataac aagcagaact tttaaaacg                                        89

<210> SEQ ID NO 57
<211> LENGTH: 125
<212> TYPE: DNA
<213> ORGANISM: Homo sapiens

<400> SEQUENCE: 57
gatctaaata tttttcagct gagttattac ggagtcatta ttctgtggta caatgctgca     60
aaaagcatca tgtggaagaa tgggaactat gcttacttta tgaagtgatg tataacacaa    120
tgaaa                                                                 125

<210> SEQ ID NO 58
<211> LENGTH: 132
<212> TYPE: DNA
<213> ORGANISM: Homo sapiens

<400> SEQUENCE: 58
ctaccccgtg actcagttac ctcccactgg gtccctccca catcatgtgg gaattgtagg     60
agctacaatt caagatgaga tttggatggg gtcacagcca aaccatatca ctgaggtatc    120
aaggagattc tt                                                         132

<210> SEQ ID NO 59
<211> LENGTH: 171
<212> TYPE: DNA
<213> ORGANISM: Homo sapiens

<400> SEQUENCE: 59
gatctgattt gctagttctt ccttgtagag ttataaatgg aaagattaca ctatctgatt     60
aatagtttct tcatactctg catataattt gtggctgcag aatattgtaa tttgttgcac    120
actatgtaac aaaacaactg aagatatgtt taataaatat tgtacttatt g              171

<210> SEQ ID NO 60
<211> LENGTH: 148
<212> TYPE: DNA
<213> ORGANISM: Homo sapiens
<220> FEATURE:
<221> NAME/KEY: unsure
<222> LOCATION: (1)
<223> OTHER INFORMATION: n = a or c or g or t.

<400> SEQUENCE: 60
ngatctttct ccttgaatat ctttcgataa acaacaaggt ggtgtgatct taatatattt     60
gaaaaaaact tcattctcgt gagtcattta aatgtgtaca atgtacacac tggtacttag    120
agtttctgtt tgattctttt ttaataaa                                        148

<210> SEQ ID NO 61
<211> LENGTH: 218
<212> TYPE: DNA
<213> ORGANISM: Homo sapiens

<400> SEQUENCE: 61

```
gatctgctag aagatggttt tggagagcac ccctttacc actgcctggt tgcagaagtg    60
ccgaaagagc actggactcc ggaaggtaac ccctcgccct ttccagaagc cagagagacc   120
aagtgttatg taagaagtag tgtcggctgt gtagaaccca tgactacaca ggccgaagtt   180
actgagaact tggacagaaa aaatagccag caagtgtt                           218
```

<210> SEQ ID NO 62
<211> LENGTH: 36
<212> TYPE: DNA
<213> ORGANISM: Homo sapiens

<400> SEQUENCE: 62

```
cattcacaca tttaacctcc ttccatacca aatctt                              36
```

<210> SEQ ID NO 63
<211> LENGTH: 106
<212> TYPE: DNA
<213> ORGANISM: Homo sapiens

<400> SEQUENCE: 63

```
gatctggaca gcagaatgtt ataacgcaag ttcatgtgtt gctcccaact ccattctctt    60
ttctctcgtg caaccagttt gcccattctc ttcctattac ttgctc                  106
```

<210> SEQ ID NO 64
<211> LENGTH: 100
<212> TYPE: DNA
<213> ORGANISM: Homo sapiens

<400> SEQUENCE: 64

```
tcagagattt gcaaagactc acgtttttgt tgttttctca tcattccatt gtgatactaa    60
gaaactaaga agcttaatga aagaaataa aatgcctatg                          100
```

<210> SEQ ID NO 65
<211> LENGTH: 190
<212> TYPE: DNA
<213> ORGANISM: Homo sapiens

<400> SEQUENCE: 65

```
gatctgcgct tccagagcgc agctatcggt gctttgcagg aggcaagtga ggcctatctg    60
gttggccttt tgaagacac caacctgtgt gctatccatg ccaaacgtgt aacaattatg    120
ccaaaagaca tccagctagc acgccgcata cgtggagaac gtgcttaaga atccactatg   180
atgggaaaca                                                          190
```

<210> SEQ ID NO 66
<211> LENGTH: 206
<212> TYPE: DNA
<213> ORGANISM: Homo sapiens

<400> SEQUENCE: 66

```
gatctgtgaa atgctatctc tcctgaagca atactgttga ccagaaagga cactccatat    60
tgtgaaaccg gcctaatttt tctgactgat atggaaacga ttgccaacac atacttctac   120
ttttaaataa acaactttga tgatgtaact tgaccttcca gagttatgga aattttgtcc   180
ccatgtaatg aataaattgt atgtat                                       206
```

PROCESS TO STUDY CHANGES IN GENE EXPRESSION IN GRANULOCYTIC CELLS

This application is a continuation of international application number PCT/US98/17284, filed Aug. 21, 1998, which claims the benefit of U.S. Provisional Application No. 60/056,844, filed Aug. 22, 1997, both of which are herein incorporated by reference in their entirety.

This application is related to application Ser. No. 08/510,032, Ser. No. 60/056,844 and application Ser. No. 08/688,514, all of which are herein incorporated by reference in their entirety. All published articles, patents and other publications cited throughout this application are herein incorporated by reference in their entirety.

TECHNICAL FIELD

This invention relates to compositions and methods useful to identify agents that modulate the response of granulocytes to inflammatory and infectious conditions.

BACKGROUND OF THE INVENTION

Granulocytes (i.e., neutrophils, eosinophils and basophils) are involved in the immune response elicited by inflammation and infection.

Inflammation

Inflammation is a localized protective response elicited by injury or destruction of tissues which serves to destroy, dilute or wall off both the injurious agent and the injured tissue. It is characterized by fenestration of the microvasculature, leakages of the elements of blood into the interstitial spaces, and migration of leukocytes into the inflamed tissue. On a macroscopic level, this is usually accompanied by the familiar clinical signs of erythema, edema, tenderness (hyperalgesia), and pain. During this complex response, chemical mediators such as histamine, 5-hydroxytryptamine, various chemotactic factors, bradykinin, leukotrienes, and prostaglandins are released locally. Phagocytic cells migrate into the area, and cellular lysosomal membranes may be ruptured, releasing lytic enzymes. All of these events may contribute to the inflammatory response.

Inflammation is initiated by, among other things, trauma, tissue necrosis, infection or immune reactions. The immediate response is temporary vasoconstriction. Vasoconstriction is followed within seconds by the acute vascular response resulting in increased blood flow (hyperemia) and edema. The acute phase is also characterized by the margination of polymorphonuclear white blood cells (neutrophils) next to endothelial cells, followed by emigration of neutrophils into the adjacent tissue. Margination is recognized by the lining up of neutrophils along the endothelium of vessels. Emigration occurs by passage of the inflammatory cells between endothelial cells.

Neutrophils

Neutrophils are the first wave of cellular attack on invading organisms and are the characteristic cells of acute inflammation. The appearance of neutrophils in areas of inflammation may be caused by chemicals released from bacteria, factors produced nonspecifically from necrotic tissue or antibody reacting with antigen. Neutrophils use an actin-rich cytoskeleton to move in a directed manner along a chemotactic gradient from the bloodstream to an inflammatory site where they ingest particles (e.g,. bacteria) and immune complexes bearing IgG (via FcR) and/or breakdown products of the complement component C3.

Neutrophils belong to a category of white blood cells known as polymorphonuclear white blood cells. The blood cells with single nuclei (mononuclear cells) form the white blood cell population that includes macrophages, T and B cells. White blood cells that contain segmented nuclei are broadly classified as polymorphonuclear. Polymorphonuclear white blood cells (or "granulocytes") are further subdivided into three major populations on the basis of the staining properties of their cytoplasmic granules in standard hematologic smears or tissue preparations: neutrophils staining pink, eosinophils staining red and basophils staining blue.

Neutrophils (also referred to as polymorphonuclear neutrophils-PMNs) make up 50% to 70% of the white blood cells (WBCs) of the peripheral blood and may be found scattered diffusely in many tissues, although they are most frequently found in areas of acute inflammation or acute necrosis. Like other WBCs, neutrophils are produced from precursor cells in the bone marrow and released into the blood when mature. After entering the circulation, neutrophils are thought to last only 1 or 2 days.

Neutrophils are characterized by numerous cytoplasmic granules that contain highly destructive enzymes that must be kept isolated from the cytoplasm. These granules contain a number of oxygen-independent enzymes as well as oxygen-dependent mechanisms of killing. Upon attraction to sites of inflammation, neutrophils attempt to engulf and digest bacteria coated with antibody and complement. Phagocytosis by neutrophils is also usually accompanied by release of the lysosomal enzymes into the tissue spaces, particularly if the organism is difficult for the neutrophil to digest At least three cytoplasmic granules are identifiable in neutrophils: specific granules containing lactoferrin, B cytochrome, the complement receptor CR3 and $\mu_2$-integrin; azurophilic granules containing acid hydrolases and other enzymes; and a third granule containing gelatinase.

In addition to the role neutrophils and other granulocytic cells play in immune response to pathogens, including bacterial infection, neutrophils and other granulocytic cells play an unwanted role in many chronic inflammatory diseases. There are many disease states in which excessive or unregulated granulocytic cell infiltration and activation are implicated in exacerbating and/or causing the disease. For instance, many inflammatory diseases are characterized by massive neutrophil infiltration, such as psoriasis, inflammatory bowel disease, Crohn's disease, asthma, cardiac and renal reperfusion injury, adult respiratory distress syndrome, rheumatoid arthritis, thrombosis and glomerulonephritis. All of these diseases are associated with increased IL-8 production which may be responsible for the chemotaxis of neutrophils into the inflammatory site.

While the role of neutrophil infiltration and activation in inflammation is well known, the biosynthetic responses of neutrophils to pathogens, chemotactic agents, proinflammatory molecules, etc. are not as well understood. Neutrophils were once thought to be in a state of terminal differentiation, thereby lacking biosynthetic ability. This view is consistent with the relative scarcity in mature circulating neutrophils of ribosomes and endoplasmic reticulum and with the ability of neutrophils to ingest particles when RNA and/or protein synthesis has been inhibited. More recently it has been demonstrated that neutrophils perform more active roles in their response to environmental stimuli.

It has thus recently been established that neutrophils synthesize de novo important macromolecules including, but not limited to interleukin (IL) 1, I1-6, I1-8, tumor necrosis factor (TNFα), granulocyte and macrophage colony-stimulating factors, interferon α (IFNα), intercellular adhesion molecule (ICAM-1) and membrane and cystoskeletal molecules, such as major histocompatibility class I antigens and actin (Beaulieu et al (1992) *J. Biolog. Chem.* 267(1):426–432; Arnold et al. (1993) *Infect. Immun.* 61(6):2545–2552; and Elsner et al. (1995) *Immunobiol* 193:456–464). No study, however, has taken a systematic approach to assess the transcriptional response during neutrophil activation via contact with a pathogen or from neutrophils isolated from a subject with a sterile inflammatory disease.

Eosinophils and Basophils

Eosinophils are another granulocytic or polymorphonuclear white blood cell that are involved in the inflammatory response. Eosinophils are found predominately in two types of inflammation: allergy and parasite infections.

The role of eosinophils in the host response to parasites is thought to be mediated through the components of the eosinophilic granules. Eosinophils are cytotoxic to schistosome larvae through an antibody-dependent cell-mediated mechanism. Eosinophil cationic proteins are highly toxic for schistosomes and may be responsible for binding of eosinophils to parasitic worms as well as fragmentation of the parasite.

The role of eosinophils in acute inflammation is not fully understood. On one hand, there is evidence that enzymes in eosinophils may serve to limit the extent of inflammation by neutralizing mediators of anaphylaxis, such as LTC4, histamine and platelet-activating factor. On the other hand, there is increasing evidence that cationic proteins in eosinophilic granules are mediators of acute inflammation. Eosinophil activation is associated with acute tissue injury and cause an intense vasoconstriction in lung microvasculature, followed by increased pulmonary vascular permeability and pulmonary edema.

Basophils or mast cells are the other major cell type characterized as a granulocytic or polymorphonuclear white blood cell. Mast cells contain granules with a variety of biologically active agents which, when released extracellularly (degranulation), cause dilation of the smooth muscle of arterioles (vasodilation), increased blood flow, and contraction of endothelial cells, thereby opening up vessel walls to permit egress of antibodies, complement or inflammatory cells into tissue spaces.

SUMMARY OF THE INVENTION

While the role of neutrophils and other granulocytic cells in inflammation and/or the immunological response to infection has been the subject of intense study, little is known about the global transcriptional response of granulocytes during cell activation. The present inventors have devised an approach to systematically assess the transcriptional response from granulocytic cells activated through contact with a pathogen or from granulocytic cells isolated from a subject with a sterile inflammatory disease.

The present invention includes a method to identify granulocytic cell genes that are differentially expressed upon exposure to a pathogen by preparing a gene expression profile of a granulocytic cell population exposed to a pathogen and comparing that profile to a profile prepared from quiescent granulocytic cells. cDNA species, and therefore genes, which are expressed de novo upon neutrophil contact with a pathogen are thereby identified. The present invention is particularly useful for identifying cytokine genes, genes encoding cell surface receptors and genes encoding intermediary signaling molecules.

The present invention also includes a method to identify granulocytic cell genes that are differentially expressed in response to a sterile inflammatory disease by preparing a gene expression profile of a granulocytic cell population isolated from a subject exhibiting the symptoms of a sterile inflammatory disease and comparing that profile to a profile prepared from granulocytic cells isolated from a normal granulocytic cell population. cDNA species, and therefore genes, which are differentially expressed in the granulocytic cells of a subject exhibiting the symptoms of a sterile inflammatory disease are thereby identified.

The present invention also includes a method to identify granulocytic cell genes that are differentially expressed upon exposure of a granulocytic cell population to an agonist (pro-inflammatory molecule) by preparing a gene expression profile of a granulocytic cell population contacted with an agonist and comparing that profile to a profile prepared from noncontacted granulocytic cells, thereby identifying cDNA species, and therefore genes, which are expressed de novo in the granulocytic cells contacted with the agonist are thereby identified.

The present invention further includes a method to identify a therapeutic or prophylactic agent that modulates the response of a granulocyte population to a pathogen, comprising the steps of preparing a first gene expression profile of a quiescent granulocyte population, preparing a second gene expression profile of a granulocyte population exposed to a pathogen, treating said exposed granulocyte population with the agent, preparing a third gene expression profile of the treated granulocyte population, comparing the first, second and third gene expression profiles and identifying agents that modulate the response of a granulocyte population to the pathogen.

Another aspect of the invention is a method to identify a therapeutic agent that modulates the expression of genes in a granulocyte population found in a subject having Another aspect of the invention includes a method to identify a therapeutic or prophylactic agent that modulates the response of a granulocyte cell population in a subject having a sterile inflammatory disease, comprising the steps of preparing a first gene expression profile of a granulocyte population in a subject having a sterile inflammatory disease, treating the granulocyte population with the agent, preparing a second gene expression profile of the treated granulocyte population, comparing the first and second gene expression profiles with the gene expression profile of a normal granulocyte population and identifying agents that modulate the expression of genes whose transcription levels are altered in the granulocyte population of the subject as compared with normal granulocyte population.

A further aspect of the present invention is a method to identify a therapeutic or prophylactic agent that modulates the response of a granulocytic population to an agonist (pro-inflammatory molecule), comprising the steps of preparing a first gene expression profile of a quiescent granulocyte population, preparing a second gene expression profile of a granulocyte population exposed to an agonist, treating the exposed granulocyte population with the agent, preparing a third gene expression profile of the treated granulocyte population, comparing the first, second and third gene expression profiles and identifying agents that modulate the response of a granulocytic population exposed to an agonist.

The present invention also includes a method of diagnosing the exposure of a subject to a pathogen, comprising the steps of preparing a first gene expression profile of a granulocyte population from the subject, comparing the first gene expression profile to a second gene expression profile of a granulocyte population exposed to that pathogen and to a third gene expression profile of a normal granulocyte preparation and diagnosing whether the subject has been exposed to a pathogen.

Another aspect of the invention includes a method of diagnosing a sterile inflammatory disease in a subject, comprising the steps of preparing a first gene expression profile of a granulocyte population from the subject, comparing the first gene expression profile to at least one second gene expression profile from a granulocyte population from a subject having a sterile inflammatory disease and to a third gene expression profile of a normal granulocyte preparation and thereby determining if the subject has a sterile inflammatory disease.

The present invention also includes a method of identifying new bacterial virulence factor genes by preparing a first gene expression profile of a quiescent granulocyte population, preparing a second gene expression profile of a granulocyte population exposed to a virulent or avirulent bacterial strain, preparing a third gene expression profile from a granulocyte population exposed to a bacterial strain with a mutation in a putative bacterial virulence factor gene, comparing the first, second and third gene expression profiles and identifying a bacterial virulence factor gene.

Another aspect of the invention is a composition comprising a grouping of nucleic acids that correspond to at least a part of one or more of the genes whose expression levels are modulated in a granulocyte population that has been exposed to a pathogen, these nucleic acids being affixed to a solid support.

Lastly, an aspect of the invention is a composition comprising a grouping of nucleic acids that correspond to at least part of one or more genes whose expression levels are modulated in a granulocyte population found in a subject having a sterile inflammatory disease, these nucleic acids being affixed to a solid support.

BRIEF DESCRIPTION OF THE DRAWINGS

FIGS. 3A and B FIG. 3 is an autoradiogram of the expression profile generated from cDNAs made with RNA isolated from neutrophils exposed to avirulent *E. coli* and virulent and avirulent *Y pestis*. All possible 12 anchoring oligo d(T)n1, n2 were used to generate a complete expression profile for the enzyme BglII.

FIG. 4 FIG. 4 represents a summary of genes which are differentially expressed in neutrophils upon exposure to virulent and avirulent *E. coli* and *Y. pestis*.

FIG. 6 is a section of an autoradiogram showing the differences in band intensity for 2 mRNA species when neutrophils are exposed to avirulent *E. coli* and virulent and avirulent *Y. pestis*.

Figure 1:
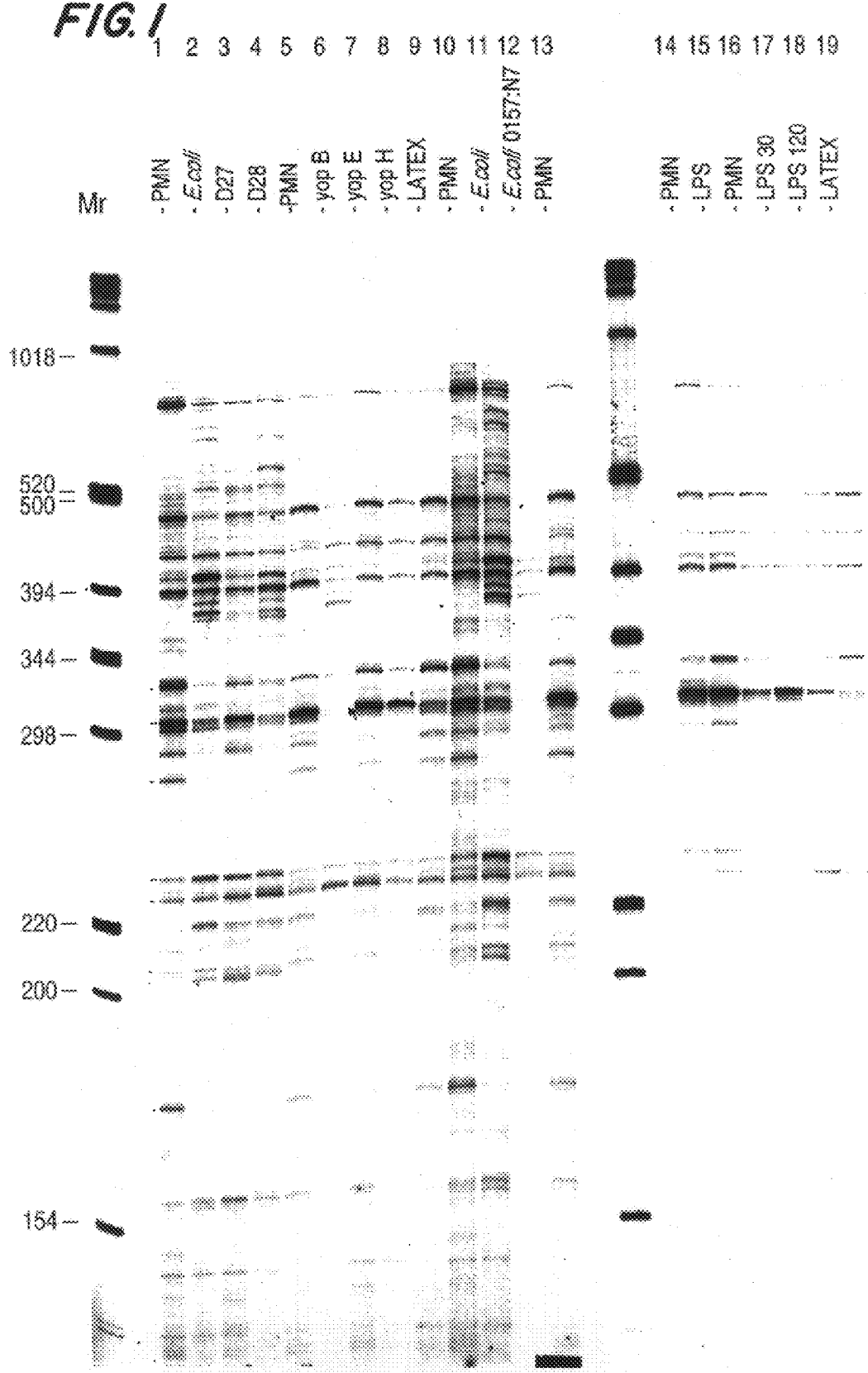
FIG. 1 FIG. 1 is an autoradiogram of the expression profile generated from cDNAs made with RNA isolated from neutrophils exposed to avirulent *Escherichia coli* and virulent and avirulent *Yersinia pestis*.

MODES OF CARRYING OUT THE INVENTION
GENERAL DESCRIPTION

The response of neutrophils to pathogens, including bacterial pathogens, is a subject of primary importance in view of the need to find ways to modulate the immune response to infection. Similarly, the response of neutrophils to agonists (pro-inflammatory molecules) is a subject of primary importance in view of the need to find better ways of controlling inflammation in various disease states. One means of assessing the response of neutrophils to pathogens and agonists is to measure the ability of neutrophils to synthesize specific RNA de novo upon contact with the pathogen or agonist.

The following discussion presents a general description of the invention as well definitions for certain terms used herein.

Definitions

Granulocytic cells, also known as polymorphonuclear white blood cells, include neutrophils, also known as polymorphonuclear neutrophils or peripheral blood neutrophils, eosinophils, and basophils, also referred to a mast cells. The term "pathogen" refers to any infectious organism including bacteria, viruses, parasites, mycoplasma, protozoans, and fungi (including molds and yeast). Pathogenic bacteria include, but are not limited to Staphylococci (e.g. aureus), Streptococci (e.g. pneumoniae), Clostridia (e.g. perfringens), Neisseria (e.g. gonorrhoeae), Enterobacteriaceae (e.g. coli as well as Klebsiella, Salmonella, Shigella, Yersinia and Proteus), Helicobacter (e.g. pylori), Vibrio (e.g. cholerae), Campylobacter (e.g. jejuni), Pseudomonas (e.g. aeruginosa), Haemophilus (e.g. influenzae), Bordetella (e.g. pertussis), Mycoplasma (e.g. pneurnoniae), Ureaplasma (e.g. urealyticum), Legionella (e.g. pneumophila), Spirochetes (e.g. Treponema, Leptospira and Borrelia), Mycobacteria (e.g. tuberculosis, smegmatis), Actinomyces (e.g. (israelii), Nocardia (e.g. asteroides), Chlamydia (e.g. trachomatis), Rickettsia, Coxiella, Ehrilichia, Rochalimaea, Brucella, Yersinia, Fracisella, and Pasteurella.

The term "sterile inflammatory disease" refers to any inflammatory disease caused by immune or nonimmune mechanisms not directly linked to infection (see Stewart et al.). Examples of sterile inflammatory diseases include, but are not limited to psoriasis, rheumatoid arthritis, glomerulonephritis, asthma, cardiac and renal reperfusion injury, thrombosis, adult respiratory distress syndrome, inflammatory bowel diseases such as Crohn's disease and ulcerative colitis and periodontal disease.

The phrase "solid support" refers to any support to which nucleic acids can be bound or immobilized, including nitrocellulose, nylon, glass, other solid supports which are positively charged and nanochannel glass arrays disclosed by Beattie (WO 95/1175). The phrase "gene expression profile", also referred to as a "differential expression profile" or "expression profile" refers to any representation of the expression of at least one mRNA species in a cell sample or population. For instance, a gene expression profile can refer to an autoradiograph of labeled cDNA fragments produced from total cellular mRNA separated on the basis of size by known procedures. Such procedures include slab gel electrophoresis, capillary gene electrophoresis, high performance liquid chromatography, and the like. Digitized representations of scanned electrophoresis gels are also included as are two and three dimensional representations of the digitized data. While a gene expression profile encompasses a representation of the expression level of at least one mRNA species, in practice, the typical gene expression profile represents the expression level of multiple mRNA species. For instance, a gene expression profile useful in the methods and compositions disclosed herein represents the expression levels of at least about 5, 10, 20, 50, 100, 150, 200, 300, 500, 1000 or more preferably, substantially all of the detectable mRNA species in a cell sample or population. Particularly preferred are gene expression profiles or arrays affixed to a solid support that contain a sufficient representative number of mRNA species whose expression levels are modulated under the relevant infection, disease, screening, treatment or other experimental conditions. In some instances a sufficient representative number of such mRNA species will be about 1, 2, 5, 10, 15, 20,25, 30, 40, 50, 50–75 or 100.

Gene expression profiles can be produced by any means known in the art, including, but not limited to the methods disclosed by: Liang et al. (1992) *Science* 257:967–971; Ivanova et al. (1995) *Nucleic Acids Res.* 23:2954–2958; Guilfoyl et al. (1997) *Nucleic Acids Res.* 25(9):1854–1858; Chee et al. (1996) *Science* 274:610–614; Velculescu et al. (1995) *Science* 270:484–487; Fischer et al. (1995) *Proc. Natl Acad. Sci. USA* 92(12):5331–5335; and Kato (1995) *Nucleic Acids Res.* 23(18):3685–3690. Preferably, gene expression profiles are produced by the methods of Prashar et al. (WO 97/05286) and Prashar et al. (1996) *Proc. Natl. Acad. Sci. USA* 93:659–663.

As an example, gene expression profiles as described herein are made to identify one or more genes whose expression levels are modulated in a granulocytic cell population exposed to a pathogen or isolated from a subject having a sterile inflammatory disease. The assaying of the modulation of gene expression via the production of a gene expression profile generally involves the production of cDNA from polyA RNA (mRNA) isolated from granulocytes as described below.

The mRNAs are isolated from a granulocytic cell source. The cells may be obtained from an in vivo source, such as a peripheral blood. As is apparent to one skilled in the art, any granulocytic cell type may be used, however, neutrophils are preferred. Furthermore, the peripheral blood cells that are initially obtained may be subjected to various separation techniques (e.g., flow cytometry, density gradients). nRNAs are isolated from cells by any one of a variety of techniques. Numerous techniques are well known (see e.g., Sambrook et al., *Molecular Cloning: A Laboratory Approach*, Cold Spring harbor Press, New York, 1987; Ausubel et., *Current Protocols in Molecular Biology*, Greene Publishing Co. New York, 1995). In general, these techniques first lyse the cells and then enrich for or purify RNA. In one such protocol. Cells are lysed in a Tris-buffered solution containing SDS. The lysate is extracted with phenol/chloroform, and nucleic acids are precipitated. Purification of poly(A)-containing RNA is not a requirement. The mnRNAs may, however, be purified from crude preparations of nucleic acids or from total RNA by chromatography, such as binding and elution from oligo (dT)-cellulose or poly(U)-Sepharose®. As stated above, other protocols and methods for isolation of RNAs may be substituted.

The mRNAs are reverse transcribed using an RNA-directed DNA polymerase, such as reverse transcriptase isolated from AMV, MoMuLV or recombinantly produced. Many commercial sources of enzyme are available (e.g., Pharmacia, New England Biolabs, Stratagene Cloning Systems). Suitable buffers, cofactors, and conditions are well known and supplied by manufacturers (see also, Sambrook et al., supra; Ausubel et al., supra).

Various oligonucleotides are used in the production of cDNA. In particular, the methods utilize oligonucleotide primers for cDNA synthesis, adapters, and primers for amplification. Oligonucleotides are generally synthesized so single strands by standard chemistry techniques, including automated synthesis. Oligonucleotides are subsequently de-protected and may be purified by precipitation with ethanol, chromatographed using a sized or reversed-phase column, denaturing polyacrylamide gel electrophoresis, high-pressure liquid chromatography (HPLC), or other suitable method. In addition, within certain preferred embodiments, a functional group, such as biotin, is incorporated preferably at the 5' or 3' terminal nucleotide. A biotinylated oligonucleotide may be synthesized using pre-coupled nucleotides, or alternatively, biotin may be conjugated to the oligonucleotide using standard chemical reactions. Other functional groups, such as florescent dyes, radioactive molecules, digoxigenin, and the like, may also be incorporated.

Partially-double stranded adaptors are formed from single stranded oligonucleotides by annealing complementary single-stranded oligonucleotides that are chemically synthesized or by enzymatic synthesis. Following synthesis of each strand, the two oligonucleotide strands are mixed together in a buffered salt solution (e.g. 1 M NaCl, 100 mM Tris-HCl pH.8.0, 10 mM EDTA) or in a buffered solution containing $Mg^2$ (e.g., 10 mM $MgCl_2$) and annealed by heating to high temperature and slow cooling to room temperature.

The oligonucleotide primer that primes first strand DNA synthesis comprises a 5' sequence incapable of hybridizing to a polyA tail of the mRNAs, and a 3' sequence that hybridizes to a portion of the polyA tail of the mRNAs and at least one non-polyA nucleotide immediately upstream of the polyA tail. The 5' sequence is preferably a sufficient length that can serve as a primer for amplification. The 5' sequence also preferably has an average G+C content and does not contain large palindromic sequence; some palindromes, such as a recognition sequence for a restriction enzyme, may be acceptable. Examples of suitable 5' sequences are CTCTCAAGGATCTACCGCT (SEQ ID NO: 1),
CAGGGTAGACGACGCTACGC (SEQ ID No: 2), and
TAATACCGCGCCACATAGCA (SEQ ID No: 3).

The 5' sequence is joined to a 3' sequence comprising sequence that hybridizes to a portion of the polyA tail of mRNAs and at least one non-polyA nucleotide immediately upstream. Although the polyA-hybridizing sequence is typically a homopolymer of dT or dU, it need only contain a sufficient number of dT or dU bases to hybridize to polyA under the conditions employed. Both oligo-dT and oligo-dU primers have been used and give comparable results. Thus, other bases may be interspersed or concentrated, as long as hybridization is not impeded. Typically, 12 to 18 bases or 12 to 30 bases of dT or dU will be used. However, as one skilled in the art appreciates, the length need only be sufficient to obtain hybridization. The non-polyA nucleotide is A, C, or G, or a nucleotide derivative, such as inosinate. If one non-polyA nucleotide is used, then three oligonucleotide primers are needed to hybridize to all mRNAs. If two non-polyA nucleotides are used, then 12 primers are needed to hybridize to all mRNAs (AA, AC, AG, AT, CA, CC, CG, CT, GA, GC, GG, GT). If three non-poly A nucleotides are used then 48 primers are needed (3×4×4). Although there is no theoretical upper limit on the number of non-polyA nucleotides, practical considerations make the use of one or two non-polyA nucleotides preferable.

For cDNA synthesis, the MRNAs are either subdivided into three (if one non-polyA nucleotide is used) or 12 (if two non-polyA nucleotides are used) fractions, each containing a single oligonucleotide primer, or the primers may be pooled and contacted with a mRNA preparation. Other subdivisions may alternatively be used. Briefly, first strand cDNA is initiated from the oligonucleotide primer by reverse transcriptase (RTase). As noted above, RTase may be obtained from numerous sources and protocols are well known. Second strand synthesis may be performed by RTase (Gubler and Hoffman, *Gene* 25: 263, 1983), which also has a DNA-directed DNA polymerase activity, with or without a specific primer, by DNA polymerase 1 in conjunction with RNaseH and DNA ligase, or other equivalent methods. The double-stranded cDNA is generally treated by phenol:chloroform extraction and ethanol precipitation to remove protein and free nucleotides. Double-stranded cDNA is subsequently digested with an agent that cleaves in a sequence-specific manner. Such cleaving agents include restriction enzymes. Restriction enzyme digestion is preferred; enzymes that are relatively infrequent cutters (e.g., ≧5 bp recognition site) are preferred and those that leave overhanging ends are especially preferred. A restriction enzyme with a six base pair recognition site cuts approximately 8% of cDNAs, so that approximately 12 such restriction enzymes should be needed to digest every cDNA at least once. By using 30 restriction enzymes, digestion of every cDNA is assured.

The adapters for use in the present invention are designed such that the two strands are only partially complementary and only one of the nucleic acid strands that the adapter is ligated to can be amplified. Thus, the adapter is partially double-stranded (i.e., comprising two partially hybridized nucleic acid strands), wherein portions of the two strands are non-complementary to each other and portions of the two strands are complementart to each other. Conceptually, the adapter is "Y-shaped" or "bubble-shaped." When the 5' region is non-paired, the 3' end of other strand cannot be extended by a polymerase to make a complementary copy. The ligated adapter can also be blocked at the 3' end to eliminate extension during subsequent amplifications. Blocking groups include dideoxynuclotides or any other agent capable of blocking the 3'-OH. In this type of adapter ("Y-shaped"), the non-complementary portion of the upper strand of the adapters is preferably a length that can serve as a primer for amplification. As noted above, the non-complementary portion of the lower strand need only be one base, however, a longer sequence is preferable (e.g., 3 to 20 bases; 3 to 15 bases; 5 to 15 bases; or 14 to 24 bases). The complementary portion of the adapter should be long enough to form a duplex under conditions of ligation.

For "bubble-shaped" adapters, the non-complementary portion of the upper strand is preferably a length that can serve as a primer for amplification. Thus, this portion is preferably 15 to 30 bases. Alternatively, the adapter can have a structure similar to the Y-shaped adapter, but has a 3' end that contains a moiety that a DNA polymerase cannot extend from.

Amplification primers are also used in the present invention. Two different amplification steps are performed in the preferred aspect. In the first, the 3' end (referenced to mRNA) of double stranded cDNA that has been cleaved and ligated with an adapter is amplified. For this amplification, either a single primer or a primer pair is used. The sequence of the single primer comprises at least a portion of the 5' sequence of the oligonucleotide primer used for first strand cDNA synthesis. The portion need only be long enough to serve as an amplification primer. The primer pair consists of a first primer whose sequence comprises at least a portion of the 5' sequence of the oligonucleotide primer as described above; and a second primer whose sequence comprises at least a portion of the sequence of one strand of the adapter in the non-complementary portion. The primer will generally contain all the sequence of the non-complementary potion, but may contain less of the sequence, especially when the non-complementary portion is very long, or more of the sequence, especially when the non-complementary portion is very short. In some embodiments, the primer will contain sequence of the complementary portion, as long as that sequence does not appreciably hybridize to the other strand of the adapter under the amplification conditions employed. for example, in one embodiment, the primer sequence comprises four bases of the complementary region to yield a 19 base primer, and amplification cycles are performed at 56° C. (annealing temperature), 72° C. (extension temperature), and 94° C. (denaturation temperature). In another embodiment, the primer is 25 bases long and has 10 bases of sequence in the complementary portion. Amplification cycles for this primer are performed at 68° C. (annealing and extension temperature) and 94° C. (denaturation temperature). By using these longer primers, the specificity of priming is increased.

The design of the amplification primers will generally follow well-known guidelines, such as average G-C content, absence of hairpin structures, inability to form primerdimers and the like. At times, however, it will be recognized that deviations from such guidelines may be appropriate or desirable.

After amplification, the lengths of the amplified fragments are determined. Any procedure that separate nucleic acids on the basis of size and allows detection or identification of the nucleic acids is acceptable. Such procedures include slap get electrophoresis, capillary gel electrophoresis, high performance liquid chromatography, and the like.

Electrophoresis is technique based on the mobility of DNA in an electric field. Negatively charged DNA migrates towards a positive electrode at a rate dependent on their total charge, size, and shape. Most often, DNA is electrophoresed in agarose or polyacrylamide gels. For maximal resolution, polyacrylamide is preferred and for maximal linearity, a denaturant, such as urea is present. A typical get setup uses a 19:1 mixture of acrylamide:bisacrylamide and a Tris-borate buffer. DNA samples are denatured and applied to the get, which is usually sandwiched between glass plates. A typical procedure can be found in Sambrook et al (*Molecular Cloning: A Laboratory Approach*, Cold Spring Harbor Press, New York, 1989) or Ausubel et al. (*Current Protocols in Molecular Biology*, Greene Publishing Co., New York, 1995). Variations may be substituted as long as sufficient resolution is obtained.

Capillary electrophoresis (CE) in its various manifestations (free solution, isotachophoresis, isoelectric focusing, polyacrylamide get. micellar electrokinetic "chromatography") allows high resolution separation of very small sample volumes. Briefly, in capillary electrophoresis, a neutral coated capillary, such as a 50 $\mu$m×37 cm column (eCAP neutral, Beckman Instruments, Calif.), is filled with a linear polyacrylamide (e.g., 0.2% polyacrylamide), a sample is introduced by high-pressure injection followed by an injection of running buffer (e.g., 1×TBE). the sample is electrophoresed and fragments are detected. An order of magnitude increase can be achieved with the use of capillary electrophoresis. Capillaries may be used in parallel for increased throughput (Smith et al. (1990) *Nuc. Acids. Res.* 18:4417; Mathies and Huang (1992) *Nature* 359:167). Because of the small sample volume that can be loaded onto a capillary, sample may be concentrated to increase level of detection. One means of concentration is sample stacking (Chien and Burgi (1992) *Anal. Chem* 64:489A). In sample stacking, a large volume of sample in a low concentration buffer is introduced to the capillary column. the capillary is then filled with a buffer of the same composition, but at higher concentration, such that when the sample ions reach the capillary buffer with a lower electric field, they stack into a concentrated zone. Sample stacking can increase detection by one to three orders of magnitude. Other methods of concentration, such as isotachophoresis, may also be used.

High-performance liquid chromatography (HPLC) is a chromatographic separation technique that separates compounds in solution. HPLC instruments consist of a reservoir of mobile phase, a pump, an injector, a separation column, and a detector. Compounds are separated by injecting an aliquot of the sample mixture onto the column. The different components in the mixture pass through the column at different rates due to differences in their partitioning behavior between the mobile liquid phase and the stationary phase. IP-RO-HPLC on non-porous PS/DVB particles with chemically bonded allyl chains can also be used to analyze nucleic acid molecules on the basis of size (Huber et al. (1993) *Anal. Biochem.* 121:351; Huber et al. (1993) *Nuc. Acids Res.* 21:1061; Huber et al. (1993) *Biotechniques* 16:898).

In each of these analysis techniques, the amplified fragments are detected. A variety of labels can be used to assist in detection. Such labels include, but are not limited to, radioactive molecules (e.g., $^{35}S$, $^{32}P$, $^{33}P$) fluorescent molecules, and mass spectrometric tags. The labels may be attached to the oligonucleotide primers or to nucleotides that are incorporated during DNA synthesis, including amplification.

Radioactive nucleotides may be obtained from commercial sources; radioactive primers may be readily generated by transfer of label from $\gamma$-$^{32}P$-ATP to a 5'-OH group by a kinase (e.g., T4 polynucleotide kinase). Detection systems include autoradiograph, phosphor image analysis and the like.

Fluorescent nucleotides may be obtained from commercial sources (e.g. ABI, Foster city, Calif.) or generated by chemical reaction using appropriately derivatized dyes. Oligonucleotide primers can be labeled, for example, using succinimidyl esters to conjugate to amine-modified oligonucleotides. A variety of florescent dyes may be used, including 6 carboxyfluorescein, other carboxyfluorescein derivatives, carboxyrhodamine derivatives, Texas red derivatives, and the like. Detection systems include photomultiplier tubes with appropriate wavelength filters for the dyes used. DNA sequence analysis systems, such as produced by ABI (Foster City, Calif.), may be used.

After separation of the amplified cDNA fragments, cDNA fragments which correspond to differentially expressed mRNA species are isolated, reamplified and sequenced according to standard procedures. For instance, bands corresponding the cDNA fragments can be cut from the electrophoresis gel, reamplified and subcloned into any available vector, including pCRscript using the PCR script cloning kit (Stratagene). The insert is then sequenced using standard procedures, such as cycle sequencing on an ABI sequencer.

An additional means of analysis comprises hybridization of the amplified fragments to one or more sets of oligonucleotides immobilized on a solid substrate. Historically, the solid substrate is a membrane, such as nitrocellulose or nylon. More recently, the substrate is a silicon wafer or a borosilicate slide. The substrate may be porous (Beattie et al. WO 95/11755) or solid. Oligonucleotides are synthesized in situ or synthesized prior to deposition on the substrate. Various chemistries are known for attaching oligonucleotide. Many of these attachment chemistries rely upon functionalizing oligonucleotides to contain a primary amine group. The oligonucleotides are arranged in an array form, such that the position of each oligonucleotide sequence can be determined.

The amplified fragments, which are generally labeled according to one of the methods described herein, are denatured and applied to the oligonucleotides on the substrate under appropriate salt and temperature conditions. In certain embodiments, the conditions are chosen to favor hybridization of exact complementary matches and disfavor hybridization of mismatches. Unhybridized nucleic acids are washed off and the hybridized molecules detected, generally both for position and quantity. The detection method will depend upon the label used. Radioactive labels, fluorescent labels and mass spectrometry label are among the suitable labels.

The present invention as set forth in the specific embodiments, includes methods to identify a therapeutic agent that modulates the expression of at least one gene in a granulocyte population. Genes which are differentially expressed during neutrophil contact with a pathogen, such as a virulent bacteria, or that are differentially expressed in a subject having a sterile inflammatory disease are of particular importance. In general, the method to identify a therapeutic or prophylactic agent that modulates the response of a granulocyte population to a pathogen, comprises the steps of preparing a first gene expression profile of a quiescent granulocyte population, preparing a second gene expression profile of a granulocyte population exposed to a pathogen, treating the exposed granulocyte population with the agent, preparing a third gene expression profile of the treated granulocyte population, comparing the first, second and third gene expression profiles and identifying agents that modulate the response of a granulocytic population to the pathogen.

In another format, the method is used to identify a therapeutic agent that modulates the expression of genes in a granulocyte population found in a subject having a sterile inflammatory disease. The general method comprises the steps of preparing a first gene expression profile of a granulocyte population in a subject having a sterile inflammatory disease, treating the granulocyte population with the agent, preparing a second gene expression profile of the treated granulocyte population, comparing the first and second gene expression profile with the gene expression profile of a normal granulocyte preparation and identifying agents that modulate the expression of genes whose transcription levels are altered in the granulocyte population of the subject as compared with normal granulocyte population.

While the above methods for identifying a therapeutic agent comprise the comparison of gene expression profiles from treated and not-treated granulocytic cells, many other variations are immediately envisioned by one of ordinary skill in the art. As an example, as a variation of a method to identify a therapeutic or prophylactic agent that modulates the response of a granulocytic population to a pathogen, the second gene expression profile of a granulocyte population exposed to a pathogen and the third gene expression profile of the treated granulocyte population can each be independently normalized using the first gene expression profile prepared from a quiescent granulocyte population. Normalization of the profiles can easily be achieved by scanning autoradiographs corresponding to each profile, and subtracting the digitized values corresponding to each band on the autoradiograph from quiescent granulocytic cells from the digitized value for each corresponding band on autoradiographs corresponding to the second and third gene expression profiles. After normalization, the second and third gene expression profils can be compared directly to detect cDNA fragments which correspond to mRNA species which are differentially expressed upon exposure of the granulocyte population to the agent to be tested.

Specific Embodiments

EXAMPLE 1

Production of gene expression profiles generated from cDNAs made with RNA isolated from neutrophils exposed to virulent and avirulent bacteria.

Expression profiles of RNA expression levels from neutrophils exposed to various bacteria offer a powerful means of identifying genes that are specifically regulated in response to bacterial infection. As an example, the production of expression profiles from neutrophils exposed to virulent and avirulent *E. coli* and *Y. pestis* allow the identification of neutrophil genes that are specifically regulated in response to bacterial infection.

Neutrophils were isolated from normal donor peripheral blood following the LPS-free method. Peripheral blood was isolated using a butterfly needle and a syringe containing 5 cc ACD, 5 cc of 6% Dextran (in normal saline). After 30 minutes of settling, plasma was collected and HBSS Hank's balcinceal salt solution (without $Ca^{++}$ or $Mg^{++}$) was added to a total volume of 40 ml. The plasma was centrifuged (1500 rpm, for 15 m at 4° C.), the supernatant decanted and cold HBSS added to resuspend the cells. The cell suspension was then layered onto a cold Ficoll Hypaq, centrifuged at 500×g for 30 m at 4° C. The pellet contains polymorphonuclear neutrophils. Neutrophils can also be isolated by other commonly used methods such as those disclosed in Current Protocols of Immunology (John Wiley & Sons, Inc.), Babior et al. (1981) In:*Leokocyte Function*, Cline, M. J. Ed., p.1–38 (Church Livingstone, N.Y.), and Haslett et al. (1985) *Am. J. Pathol.* 119:101–110.

Following isolation, neutrophils were incubated with *E. coli* or *Y. pestis*. Before incubation, bacteria are harvested and washed in phosphate buffered saline and opsonized either autologous human serum or complement factor C7 deficient human serum (SIGMA). Incubation was at a ratio of approximately a PMN:bacteria ratio of 1:20 in RPMI 1640 (HEPES buffered) with heat inactivated Fetal Bovine Serum at 37° C. with gentle mixing in a rotary shaker bath As controls, neutrophils were incubated with either bacterial lipopolysaccharide (LPS) or latex beads. LPS was added to approximately $3.38 \times 10^8$ cells in 100 ml of RPMI Roswell Park. Memorial Institute containing 6% autologous serum to a final concentration of 1 ng/ml to 1 μg/l. Incubation proceeded for 30 or 120 minutes with gentle rotation in disposable polycarbonate Erlenmeyer flasks at 37° C. After incubation, the cells were spun down and washed once with HBSS.

Total cellular RNA was prepared from untreated and treated neutrophils are described above using the procedure of Newburger et al.(1981) *J. Biol. Chem.* 266(24): 16171–7 and Newburger et al. (1988) *Proc. Natl. Acad Sci USA* 85:5215–5219. Ten micrograms of total RNA, the amount obtainable from about $3 \times 10^6$ neutrophils, is sufficient for a complete set of cDNA expression profiles.

Synthesis of cDNA was performed as previously described by Prashar et al. in WO 97/05286 and in Prashar et al. (1996) *Proc. Natl. Acad. Sci. USA* 93:659–663. Briefly, cDNA was synthesized according to the protocol described in the GIBCO/BRL kit for cDNA synthesis. The reaction mixture for first-strand synthesis included 6 μg of total RNA, and 200 ng of a mixture of 1-base anchored oligo(dT) primers with all three possible anchored bases (ACGTAATACGACTCACTATAGGGCGAATTGGGTC GACTTTTTTTTTTTTTT TTn1 wherein n1=A/C or G, SEQ ID NO: 4) along with other components for first-strand synthesis reaction except reverse transcriptase. This mixture was incubated at 65° C. for 5 m, chilled on ice and the process repeated. Alternatively, the reaction mixture may include 10 g of total RNA, and 2 pmol of 1 of the 2-base anchored oligo(dT) primers a heel such as RP5.0 (CTCTCAAGGATCTTACCGCTT $_{18}$AT, SEQ ID NO: 5), or RP6.0 (TAATACCGCGCCACATAGCAT $_{18}$CG, SEQ ID NO: 6), or RP9.2

(CAGGGTAGACGACGCTACGCT $_{18}$GA, SEQ ID NO: 7) along with other components for first-strand synthesis reaction except reverse transcriptase. This mixture was then layered with mineral oil and incubated at 65° C. for 7 min followed by 50° C. for another 7 min. At this stage, 2 μl of Superscript reverse transcriptase (200 units/μl; GIBCO/BRL) was added quickly and mixed, and the reaction continued for 1 hr at 45–50° C. Second-strand synthesis was performed at 16° C. for 2 hr. At the end of the reaction, the cDNAs were precipitated with ethanol and the yield of cDNA was calculated. In our experiments, ≈200 ng of cDNA was obtained from 10 μg of total RNA.

The adapter oligonucleotide sequences were

A1 (TAGCGTCCGGCGCAGCGACGGCCAG, SEQ ID NO: 8) and

A2 (GATCCTGGCCGTCGGCTGTCTGTCGGCGC, SEQ ID NO: 9). One microgram of oligonucleotide A2 was first phosphorylated at the 5' end using T4 polynucleotide kinase (PNK). After phosphorylation, PNK was heated denatured, and 1 μg of the oligonucleotide A1 was added along with 10× annealing buffer (1 M NaCl/100 mM Tris-HCl, pH8.0/10 mM EDTA, pH8.0) in a final vol of 20 μl. This mixture was then heated at 65° C. for 10 min followed by slow cooling to room temperature for 30 min, resulting in formation of the Y adapter at a final concentration of 100 ng/μl. About 20 ng of the cDNA was digested with 4 units of Bgl II in a final vol of 10 μl for 30 min at 37° C. Two microliters (≈4 ng of digested cDNA) of this reaction mixture was then used for ligation to 100 ng (≈50-fold) of the Y-shaped adapter in a final vol of 5 μl for 16 hr at 15° C. After ligation, the reaction mixture was diluted with water to a final vol of 80 μl (adapter ligated cDNA concentration, ≈50 pg/μl) and heated at 65° C. for 10 min to denature T4 DNA ligase, and 2 μl aliquots (with 100 pg of cDNA) were used for PCR.

The following sets of primers were used for PCR amplification of the adapter ligated 3'-end cDNAs:

TGAAGCCGAGACGTCGGTCG(T)$_{18}$ n1, n2 (wherein n1, n2=AA, AC, AG AT CA CC CG CT GA GC GG and GT, SEQ ID NO: 10) as the 3' primer with A1 as the 5' primer or alternatively RP 5.0, RP 6.0, or RP 9.2 used as 3' primers with primer A1.1 serving as the 5' primer. To detect the PCR products on the display gel, 24 pmol of oligonucleotide A1 or A1.1 was 5'-end-labeled using 15 μl of [γγ-$^{32}$ P]ATP (Amersham; 3000 Ci/mmol) and PNK in a final volume of 20 μl for 30 min at 37° C. After heat denaturing PNK at 65 ° C. for 20 min, the labeled oligonucleotide was diluted to a final concentration of 2 μM in 80 μl with unlabeled oligonucleotide A1.1. The PCR mixture (20 μl) consisted of 2 μl (≈100 pg) of the template, 2 μl of 10× PCR buffer (100 mM Tris.HCl, pH 8.3/500 mM KCl), 2 μl of 15 mM MgCl₂ to yield 1.5 mM final Mg²⁺ concentration optimum in the reaction mixture, 200 μM dNTPs, 200 nM each 5' and 3' PCR primers, and 1 unit of Amplitaq Gold. Primers and dNTPs were added after preheating the reaction mixture containing the rest of the components at 85° C. This "hot start" PCR was done to avoid artefactual amplification arising out of arbitrary annealing of PCR primers at lower temperature during transition from room temperature to 94° C. in the first PCR cycle. PCR consisted of 5 cycles of 94° C. for 30 sec, 55° C. for 2 min, and 72° C. for 60 sec followed by 25 cycles of 94° C. for 30 sec, 60° C. for 2 min, and 72° C. for 60 sec. A higher number of cycles resulted in smeary gel patterns. PCR products (2.5 μl) were analyzed on 6% polyacrylamide sequencing gel. For double or multiple digestion following adapter ligation, 13.2 μl of the ligated cDNA sample was digested with a secondary restriction enzyme(s) in a final vol of 20 μl. From this solution, 3 μl was used as template for PCR. This template vol of 3 μl carried ≈100 pg of the cDNA and 10 mM MgCl₂ (from the 10×enzyme buffer), which diluted to the optimum of 1.5 mM in the final PCR vol of 20 μl. Since Mg²⁺ comes from the restriction enzyme buffer, it was not included in the reaction mixture when amplifying secondarily cut cDNA. Bands were extracted from the display gels as described by Liang et al. (1995 Curr. Opin. Immunol. 7:274–280), reamplified using the 5' and 3' primers, and subcloned into pCR-Script with high efficiency using the PCR-Script cloning kit from Stratagene. Plasmids were sequenced by cycle sequencing on an ABI automated sequencer.

FIG. 1 presents an autoradiogram of the expression profile generated from cDNAs made from RNA isolated from control (untreated) neutrophils (lanes 1, 5, 10, 13, 14 and 16), neutrophils incubated with avirulent E. coli K12 (lanes 2 and 11), virulent Y. pestis D27 (lane 3), avirulent Y. pestis D28 (lane 4), Y. pestis yopB (lane 6), Y. pestis yopE (lane 7), Y. pestis yoph (lane 8), latex beads (lanes 9 and 19), virulent Entero Hemorrhagic E. coli (EHEC) (lane 12), LPS (lane 15), 1 ng/ml LPS for 30 minutes (lane 17), and LPS for 120 minutes (lane 18). The anchoring oligo d(T)18 n1, n2 has A and C at the n1 and n2 positions, respectively. The cDNAs were digested with BglII.

EXAMPLE 2

Production of gene expression profiles generated from cDNAs made with RNA isolated from neutrophils exposed to virulent and avirulent bacteria and neutrophils exposed to cytokines.

Neutrophils were isolated from normal donor peripheral blood following the LPS-free method as set forth in Example 1.

Neutrophils were incubated with virulent and avirulent E. coli or Y. pestis, LPS at 1 ng/ml, GM-CSF at 100 units/ml, TNFa at 1000 units/ml, or γIFN at 100 units/ml. The bacterial cells, LPS or cytokines were added to approximately 3.38×10⁸ cells in 100 ml of RPMI containing 6% H1 autologous serum. Incubation proceeded for 2 to 4 hours, preferably 2 hours, with gentle rotation in disposable polycarbonate Erlenmeyer flasks at 37° C. After incubation, the cells were spun down and washed once with HBSS.

After incubation of the neutrophils, RNA was extracted and the cDNA profiles prepared as described in Example 1.

Figure 2:
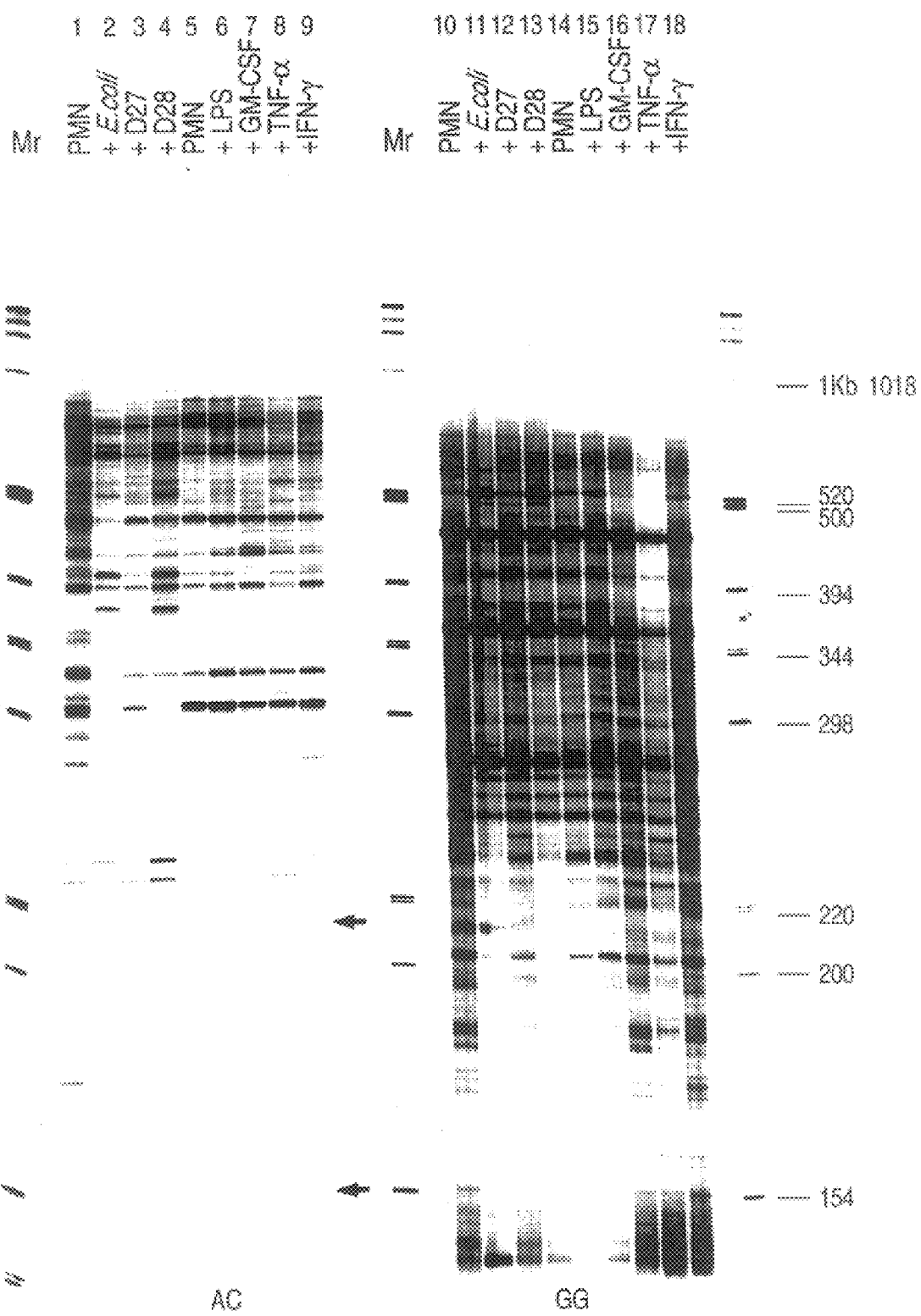
FIG. 2 FIG. 2 is an autoradiogram of the expression profile generated from cDNAs made with RNA isolated from neutrophils exposed to virulent and avirulent *E. coli*, virulent and avirulent *Y. pestis*, LPS, GM-CSF, TNFc, or γIFN.
Figure 5A:
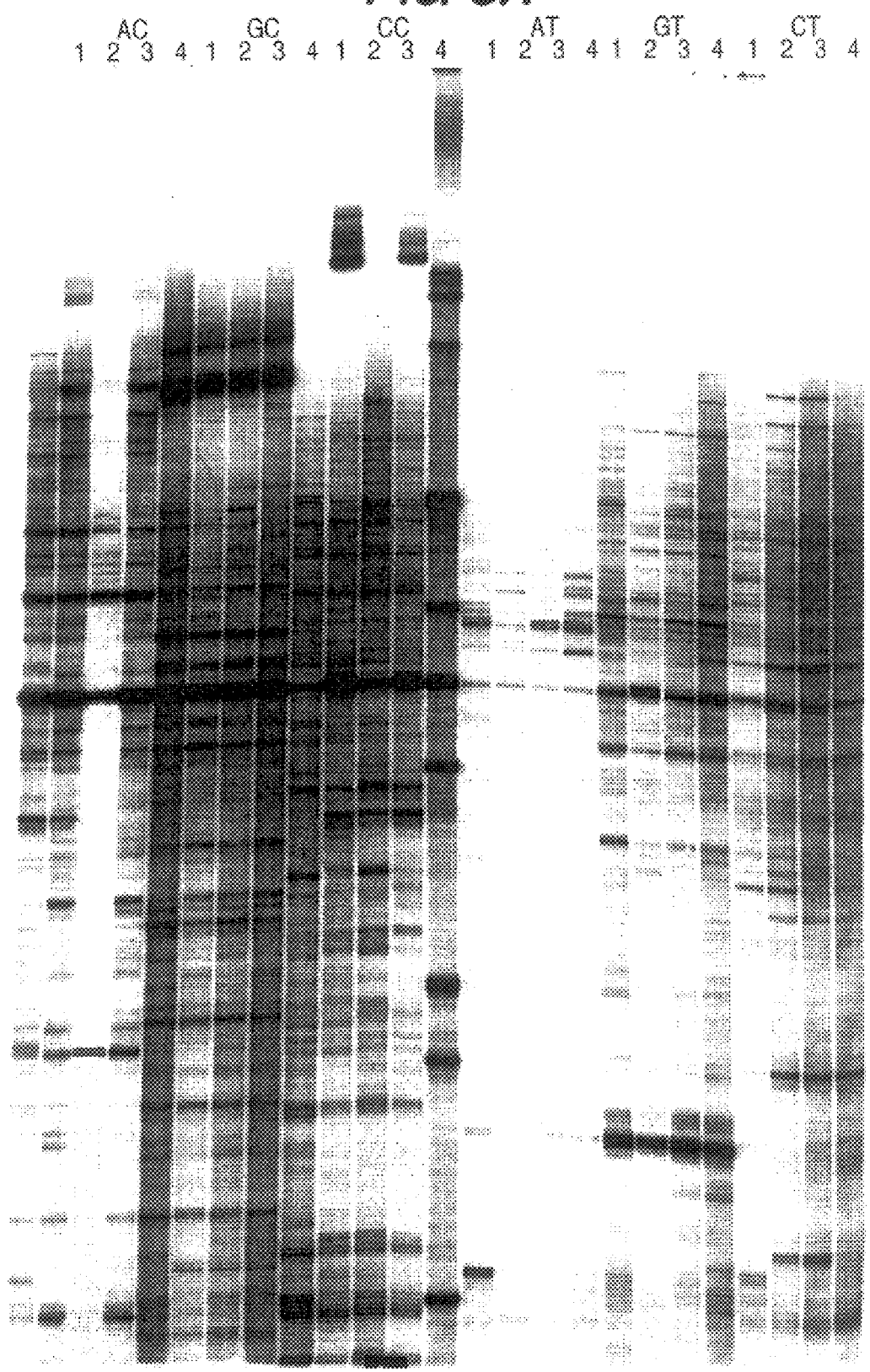
FIG. 5 FIG. 5 is an autoradiogram of the expression profile generated from cDNAs made with RNA isolated from neutrophils exposed to avirulent *E. coli* and virulent and avirulent *Y. pestis*. All possible 12 anchoring oligo d(T)n1, n2 were used to generate a complete expression profile for the enzyme BamHI.
Figure 5B:
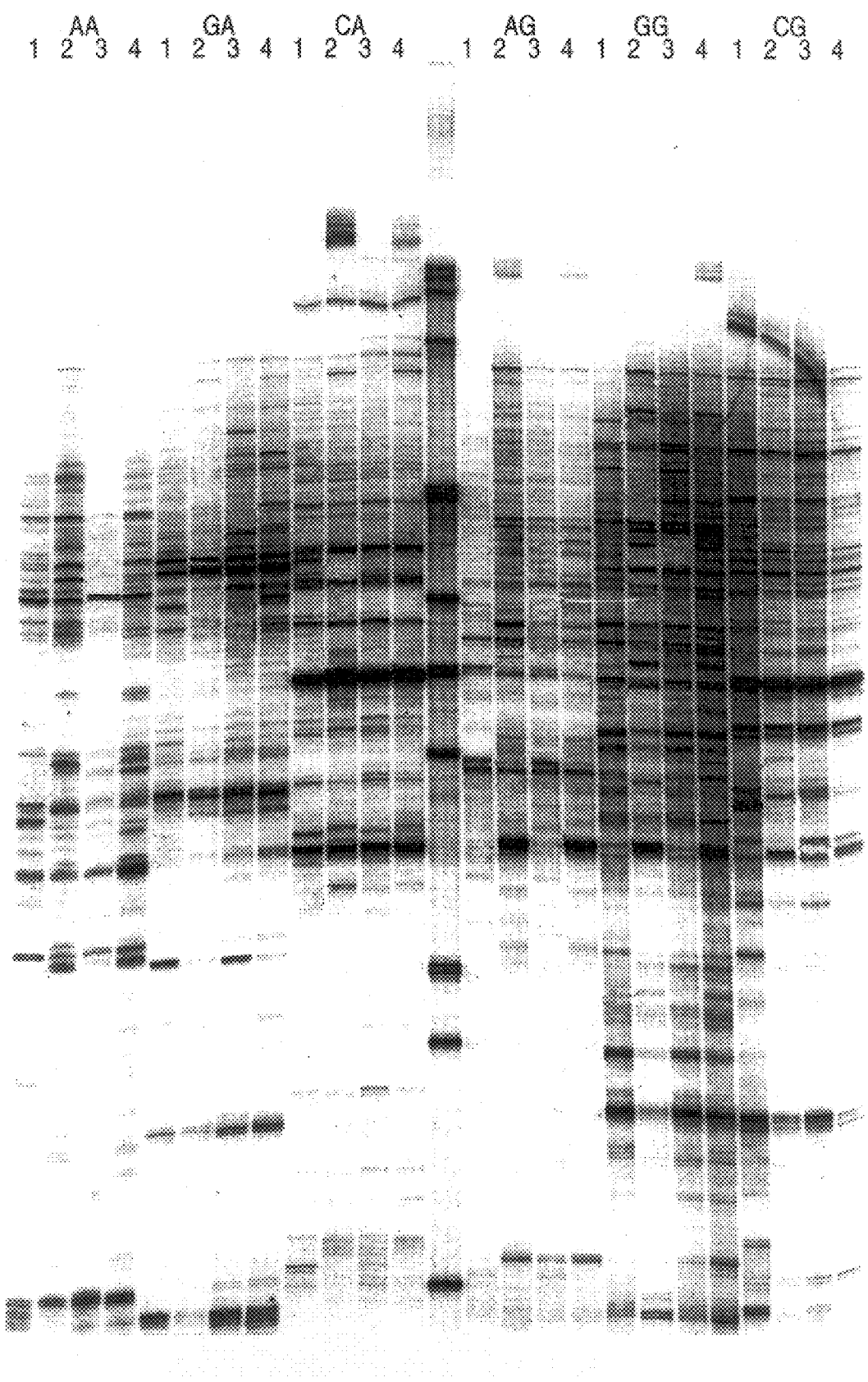

FIG. 2 is an autoradiogram of the expression profiles generated from cDNAs made with RNA isolated from control (untreated) neutrophils (lanes 1, 5, 10 and 14), neutrophils incubated with avirulent E. coli K12 (lanes 2 and 11), virulent Y. pestis (lanes 3 and 12), avirulent Y. pestis (lanes 4 and 13), 1 ng/ml LPS (lanes 6 and 15), 100 units/ml GM-CSF(lanes 7 and 16), 1000 units/ml TNFα (lanes 8 and 17) and 100 units/ml γIFN (lanes 9 and 18). The anchoring oligo d(T)18n1, n2 has A and C at the n1 and n2 positions for lanes 1–9 and G and G at the n1 and n2 for lanes 10–18. The cDNAs were digested with BglII.

As exhibited by FIG. 2, the differential expression of mRNA species (as exhibited by cDNA fragments) in neutrophils exposed to virulent and avirulent E. coli and Y. pestis is not equivalent to the differential expression of mRNA species in neutrophils exposed to the various cytokines.

EXAMPLE 3

Production of gene expression profiles generated from cDNAs made with RNA isolated from neutrophils exposed to bacteria using all 12 possible anchoring oligo d(T) n1, n2.

Neutrophils were isolated from normal donor peripheral blood following the LPS-free method.

Neutrophils were incubated with E. coli or Y. pestis.

After incubation of the neutrophils, RNA was extracted and the cDNA profiles prepared as described in Example 1. FIG. 3 is an autoradiogram of the expression profiles generated from cDNAs made with RNA isolated from control (untreated) neutrophils (lane 1), neutrophils incubated with avirulent E. coli K12 (lane 2), virulent Y. pestis (lane 3), avirulent Y. pestis (lane 4). The anchoring oligo d(T)18 n1and n2 positions are indicated at the top of the figure. The cDNAs were digested with BglII.

FIG. 4 represents a summary of genes which are differentially expressed in neutrophils upon exposure to virulent and avirulent E. coli and Y. pestis. Expression patterns are determined by visual examination of the autoradiography gels comparing band intensity between neutrophils exposed to the various bacteria. The autoradiography gels can also be scanned using commonly available equipment, such s a UMAX D-1L scanner. Bands which exhibit altered intensities in gene expression profiles from neutrophils exposed to the various bacteria when compared to the gene expression profile prepared from normal nonexposed neutrophils are then extracted from the display gel as previously described by in Example 1. The isolated fragments are then reamplified using 5' and 3' primers, subcloned into pCR-Script (Stratagene) and sequenced using an ABI automated sequencer.

Tables 1 and 2 represent a summary of cDNA bands which are differentially expressed in response to exposure to E. coli.

TABLE 1

| Clones | mRNA Expression Pattern | Control | 10' | 30' | 60' | 120' | n1n2 | Sequenced by | Closest Genbank Acc. # | Closest Homology |
|---|---|---|---|---|---|---|---|---|---|---|
| 846 | Up | 0 | 0 | +− | 2+ | 4+ | AA | Yale | K02286 | Urokinase Gene |
| 847 | Up | +− | +− | +− | + | 2−3+ | AA | Yale | | |
| 848 | Up | +− | +− | 0 | +− | 2+ | AA | Yale | | |
| 849 | Up | +− | +− | +− | +− + | 1−2+ | AA | Yale | | |
| 850 | Down | + | 0 | 0 | 0 | 0 | AA | Yale | | |
| 851 | Up | 0 | 0 | 0 | 0 | + | AA | Yale | | |
| 852 | Down | + | + | +− | + | 0 | AA | Yale | | |
| 853 | Up | 0 | 0 | +− | +− | 1−2+ | AA | Yale | | |
| 854 | Down | 2+ | + | +− | 0 | 0 +− | AA | Yale | AF039715 | C. elegans cosmidR0 6A10 |
| T103 | Up | 3+ | 3+ | 3−4+ | 4−5+ | 4−5+ | AA | Yale | M77693 | HUMAN SSAT |
| 855 | Up | +− | +− | +− | +− | 2+ | AA | Yale | G29248 | Human STS SHGC 17036 |
| 856 | Up | +− | +− | +− | +− | 2+ | AA | Yale | AI038932 | ox96ho8.xi soares senescent Fibroblasts |
| T104 | Up | + | + | +− | + | 2+ | AA | Yale | AA931109 | HUMAN CGAP KID3 |
| T105 | | 3−4+ | 3−4+ | 3−4+ | 3+ | 3+ | AA | Yale | M11354 | HUMAN H3.3 HISTONE |
| 857 | | + | + | 2+ | + | +− | AA | Yale | | |
| T107 | Down | 2−3+ | 2−3+ | 2−3+ | 2−3+ | 2+ | AA | Yale | AA936257 | on43e12 sineI CGAP co8 |
| 858 | Down | 2+ | 2+ | 2+ | 2+ | + +− | AA | Yale | | |
| 859 | Up | +− | +− | +− | 2+ | 1−2+ | AA | Yale | AC004987 | DJ1173I2 0 Clone |
| 860 | Down | 2−3+ | 2−3+ | 2+ | 2+ | +− | AA | Yale | | |
| 861 | Down | + | + | 1−2+ | +− | +− | AA | Yale | | |
| 862 | | 2−3+ | 2−3+ | 2−3+ | 2−3+ | 2−3+ | AA | Yale | | |
| 863 | Down | 2+ | + | +− | + | + | AA | Yale | H26311 | Cystic Fibrosis Antigen |
| 864 | Up | 2+ | 2+ | 2+ | 2−3+ | 2−3+ | AA | Yale | | |
| 865 | Up | + | + | 2+ | 2−3+ | 2+ | AA | Yale | | |
| 866 | Up | +− | +− | + | + | 2+ | AA | Yale | G06511 | Human STS WI-7311 |
| 867 | Down | 2+ | 2+ | 2+ | 2+ | 1−2+ | AA | Yale | | |
| 868 | | +− | +− | + | 2+ | +− | AA | Yale | | |
| 869 | Up | + | +− | +− | +− | 2+ | AC | Yale | | |
| 870 | Up | 0 | 0 | 0 | +− | 1−2+ | AC | Yale | | |
| 871 | Down | 1−2+ | 1−2+ | 1−2+ | + | +− | AC | Yale | AI026899 | ov42do7.xI Soares testis nht |
| 872 | | + | + | +− | + | + | AC | Yale | AA916304 | on22do4.si NCI CGAP Lu5 |
| 873 | Up | +−_+ | +−_+ | +−_+ | +−_+ | 2+ | AC | Yale | | |
| 874 | Up | 1−2+ | 1−2+ | 1−2+ | + | 3+ | AC | Yale | AI012139 | EST 206590 (Rat Placenta) |
| 875 | Up | 1−2+ | 1−2+ | + | + | 2−3+ | AC | Yale | | |
| 876 | Down | + | 1−2+ | 2+ | 1−2+ | +−_0 | AC | Yale | AI031728 | ow39a05.xI Soares parathyroid tumor NGHPA |
| 877 | Down | 2−3+ | 2+ | 2+ | + | +− | AC | Yale | | |
| 878 | Down | 2−3+ | 2−3+ | 2+ | 1−2+ | 0_+− | AC | Yale | AB002384 | human mRNA for KIAA0386 gene |

TABLE 1-continued

| Clones | mRNA Expression Pattern | Control | 10' | 30' | 60' | 120' | n1n2 | Sequenced by | Closest Genbank Acc. # | Closest Homology |
|---|---|---|---|---|---|---|---|---|---|---|
| 879 |  | + | +− | 0 | 0 | + | AC | Yale | | |
| 880 | Down | 1−2+ | +− | +− | +− | 0 | AC | Yale | AI016473 | Transcription Factor BTF3 |
| 881 | Down | + | + | 1−2+ | + | +− | AC | Yale | U82275 | Human immuno-globulin-like transcript |
| 882 | Up | 2+ | 2+ | 3+ | 3−4+ | 4+ | AC | Yale | AI016664 | Diamineacetyl Transferase |
| 883 | Down | 1−2+ | + | + | + | +− | AC | Yale | AA909168 | .SI Soares NFLT GBC.SI |
| 884 | Down | + | +− | 0 | 0 | 0 | AC | Yale | AI039973 | ox88e09.si Soares senescent fibroblasts |
| 885 | Up | 2+ | 1−2+ | 1−2+ | 2+ | 2−3+ | AC | Yale | AI026998 | ow41d06.si Soares parathyroid tumor NB4PA |
| 886 |  | 0 | +− | +−_+ | +− | 0 | AC | Yale | | |
| 887 | Up | +− | + | + | +− | + | AC | Yale | | |
| 888 | Up | 0 | 0 | 0 | +− | + | AC | Yale | | |
| T7 | Down | 2+ | 1−2+ | 1−2+ | + | +− | AC | Yale | | |
| 889 | Up | +− | 0 | +− | +− | 1−2+ | AC | Yale | | |
| T8 | Down | 2−3+ | 2+ | 2+ | 2+ | 1−2+ | AC | Yale | G06680 | HUMAN STS |
| 890 | Up | 2+ | 2+ | 1−2+ | + | +− | AC | Yale | | |
| 891 | Down | + | + | +− | 0 | 0 | AC | Yale | | |
| T76 | Down | 2−3+ | 2+ | 2+ | 1−2+ | +− | AC | Yale | S73591 | HUMAN H HCPA78 HOMOLOG |
| 892 | Down | 3+ | 3+ | 3+ | 2+ | +− | AC | Yale | | |
| 893 |  | 2+ | + | 1−2+ | 2+ | 2+ | AC | Yale | | |
| T98 | Down | 2−3+ | 2−3+ | 2−3+ | 2−3+ | +_+− | AC | Yale | G06788 | HUMAN STS |
| 894 | Down | 2+ | 1−2+ | 1−2+ | 1−2+ | + | AC | Yale | AF039656 | Neuronal tissue-enrichedacidic protein |
| 895 | Down | 2−3+ | 2−3+ | 2−3+ | 2+ | +− | AC | Yale | AI016303 | ot72do7.si soares total Fetus Nb3hf8 |
| 896 | Down | 2+ | 2+ | 1−2+ | +− | 0 | AC | Yale | AC004987 | DJ 1173I20 clone |
| T81 | Up | 0 | 0 | 0 | 0 | 3+ | AC | Yale | AA926999 | om26do7 si Soares NFLTG3c 1s1 |
| T82 | Up | + | + | + | +− | 2−3+ | AC | Yale | AA926999 | om26d07.SI NFL TG3cSi |
| T83 | Down | 2+ | 2+ | 1−2+ | 1−2+ | 1−2+ | AC | Yale | | |
| T84 |  | 2−3+ | 2+ | 2−3+ | 3+ | 2−3+ | AC | Yale | | |
| T85 | Down | + | +− | +−_0 | +−_0 | 0 | AC | Yale | O89052 | HUMAN PROTONATPASE |
| 897 | Down | 2+ | 1−2+ | 1−2+ | + | +_+− | AC | Yale | | |
| 898 |  | 2+ | 2+ | 2+ | 2+ | AC | Yale | | | |
| 899 | Up | 0 | 0 | +− | + | 3+ | AC | Yale | | |
| 900 | Down | 1−2+ | 1−2+ | +− | 1−2+ | 0 | AC | Yale | | |
| 901 | Up | 1−2+ | + | 1−2+ | 2+ | 2−3+ | AC | Yale | | |
| 902 | Down | 2+ | + | 1−2+ | 1−2+ | + | AC | Yale | | |
| 903 | Down | 2+ | 2+ | 3+ | 3−4+ | +− | AC | Yale | | |
| 904 |  | + | + | +− | +− | + | AC | Yale | | |
| 905 | Up | 0 | +− | 0 | + | 3−4+ | AG | Yale | KO2286 | Human urokinase gene 3' end |
| 906 | Up | 0 | 0 | +− | +− | 1−2+ | AG | Yale | | |
| T111 |  | +−_+ | 2+ | +− | +− | +− | AG | Yale | | |
| 907 |  | +− | + | + | 2+ | +− | AG | Yale | | |
| 908 | Down | 2+ | 2+ | 1−2+ | 2+ | +− | AG | Yale | | |

TABLE 1-continued

| Clones | mRNA Expression Pattern | Control | 10' | 30' | 60' | 120' | n1n2 | Sequenced by | Closest Genbank Acc. # | Closest Homology |
|---|---|---|---|---|---|---|---|---|---|---|
| 909 | | +- | +- | + | 2+ | +-_0 | AG | Yale | | |
| 910 | Down | + | 1-2+ | 0 | +- | +- | AG | Yale | AC002091 | Genomic Sequence Human 17, complete sequence |
| 911 | Down | 2+ | 2+ | 2+ | + | - | AG | Yale | | |
| T113 | Down | 2+ | 2-3+ | 2+ | 2+ | 1-2+ | AG | Yale | AI039523 | 0x371002.si Soares total fetus NB22HF8 |
| 912 | Down | +- | +- | +- | - | - | AG | Yale | | |
| 913 | Down | 3+ | 3+ | 2-3+ | 2-3+ | 2+ | AG | Yale | | |
| 914 | Up | - | +- | - | - | + | AG | Yale | | |
| 915 | Up | + | 1-2+ | + | 1-2+ | 2+ | AG | Yale | AI038932 | 'ox96h08.xi Soares senescent fibroblasts |
| T115 | | 2+ | 2+ | 2+ | 2+ | 2+ | AG | Yale | | |
| 916 | Up | + | + | + | + | 2+ | AG | Yale | AC005038 | Homosapiens clone NH 048666I22 HTGS phase 1 |
| 917 | Down | +- | +- | - | - | - | AG | Yale | | |
| 918 | Down | + | + | + | + | +- | AG | Yale | | |
| 919 | | + | + | - | + | + | AG | Yale | | |
| 920 | Down | + | 2+ | + | +- | +- | AG | Yale | | |
| T116 | Down | 3-4+ | 3-4+ | 3+ | 3+ | 3+ | AG | Yale | M11353 H | Histone H3.3 (human) |
| T117 | Up | + | + | + | 2+ | 2+ | AG | Yale | | |
| 921 | Up | 1-2+ | 2+ | + | 1-2+ | 2-3+ | AG | Yale | AA912471 | NCI CGAP GC4 Homo Sapiens |
| 922 | Down | 1-2+ | 2+ | + | 1-2+ | 0-+-? | AG | Yale | | |
| 923 | Down | +- | +- | - | +- | - | AG | Yale | | |
| 924 | Up | 0 | 0 | 0 | +- | 2+ | AG | Yale | | |
| 925 | Down | +- | + | 0 | 0 | 0 | AG | Yale | | |
| 926 | Down | 1-2+ | 1-2+ | + | +-_+ | 2+ | AG | Yale | | |
| 927 | Up | + | ?+ | ?+ | 2+ | 2+ | AG | Yale | AA917380 | 0180a04.si NCI CGAP KIDS |
| 928 | Up | 0 | 0 | 0 | 0 | 2+ | AG | Yale | AA926999 | Homo Soares NFL TGBC si |
| 929 | Down | + | - | + | + | - | AG | Yale | | |
| 930 | Up | 0 | 0 | 0 | +- | 2+ | AG | Yale | CH29R28051 | AD000864 HomoSapiens DNA from chromosome 19 cosmid R28051 |
| 931 | Down | 2+ | 2+ | 1-2+ | 1-2+ | + | AG | Yale | | |
| 932 | Up | + | + | + | + | 2+ | AG | Yale | | |
| 933 | Down | 4+ | 4+ | 3+ | 3+ | 3+ | AG | Yale | m81637 | Human grancalan mRNA |
| 934 | | - | - | +- | + | +- | AG | Yale | | |
| 935 | Down | +- | + | + | + | - | AG | Yale | | |
| 936 | | + | +- | +- | + | + | AG | Yale | | |
| 937 | Up | +- | +- | +- | +- | + | AG | Yale | | |
| 938 | Up | +- | +- | + | 2+ | AT | Yale | | | |
| 939 | Up | 0 | 0 | +- | +- | 2+ | AT | Yale | AA916304 | NCI CGAP LU5 HOMO SAPIENS |
| 940 | | + | + | 2+ | 2-3+ | + | AT | Yale | | |
| 941 | Up | + | + | + | + | 2-3+ | AT | Yale | | |
| 942 | Up | + | + | +- | 0 | 1-2+ | AT | Yale | | |

TABLE 1-continued

| Clones | mRNA Expression Pattern | Control | 10' | 30' | 60' | 120' | n1n2 | Sequenced by | Closest Genbank Acc. # | Closest Homology |
|---|---|---|---|---|---|---|---|---|---|---|
| 943 | Down | +− | +− | +− | + | − | AT | Yale | | |
| 944 | Down | 2+ | + | + | +− | 0 | AT | Yale | | |
| 945 | Up | + | +−_+ | +−_+ | +−_+ | 2+ | AT | Yale | AA928171 | ON86HO3 SOARES NFL TGBC SI |
| 946 | Down | + | + | + | − | − | AT | Yale | | |
| 947 | | 0 | 0 | + | 2+ | 0 | AT | Yale | | |
| 948 | Down | + | + | + | +− | − | AT | Yale | | |
| 949 | Up | 0 | 0 | 0 | 0 | 1−2+ | AT | Yale | AI038932 | HOMO SAPIENS SOARES SENESCENT FIBROBLASTS |
| 950 | Down | 2−3+ | 2−3+ | 2−3+ | 2−3+ | +? | AT | Yale | | |
| 951 | Up | +− | +− | +− | +− | + | AT | Yale | | |
| 952 | Up | 0 | 0 | 0 | +− | 1−2+ | AT | Yale | ACC004551 | HOMO SAPIENS HTGS PHASE 1 |
| 953 | Down | 1−2+ | + | 1−2+ | +− | 0 | AT | Yale | | |
| 954 | Up | + | + | + | 1−2+ | 2−3+ | AT | Yale | AI026998 | HOMO SAPIENS SOARES PARATHYROID TUMOR |
| 955 | Down | + | + | + | + | 0 | AT | Yale | | |
| 956 | Up | +− | +− | +− | +− | + | AT | Yale | | |
| 957 | Down | 2+ | 2+ | 2+ | 2+ | + | AT | Yale | | |
| 958 | Up | + | + | + | +−_+ | 2+ | AT | Yale | | |
| T123 | Up | +− | +− | + | 2+ | 3+ | AT | Yale | HSO27467 | HUMAN BCL-2 RELATED (BF1-1) MRNA |
| 959 | | + | +_+− | 2+ | + | + | AT | Yale | | |
| 960 | Down | 2+ | + | + | + | +− | AT | Yale | | |
| 961 | | 0 | +− | 2+ | +−_0 | | AT | Yale | | |
| 962 | Up | 0 | 0 | 0 | 0 | 2+ | AT | Yale | | |
| T124 | Up | 3+ | 3+ | 3+ | 3−4+ | 3−4+ | AT | Yale | | |
| 963 | Down | 2+ | 2+ | 2+ | 2+ | + | AT | GLI | | |
| 964 | | +− | 1−2+ | + | + | +− | AT | GLI | | |
| 965 | UP | 0 | 0 | +− | 2+ | 1−2+ | AT | GLI | | |
| 966 | Down | + | + | + | 1−2+ | +− | AT | GLI | | |
| 967 | Down | 3+ | 3+ | 3+ | 3+ | +− | AT | GLI | M60830 | Human gene EVI2B#P |
| 968 | Down | + | + | 2+ | 1−2+ | +− | AT | GLI | | |
| 969 | Up | 0 | 0 | 0 | +− | 2+ | AT | GLI | | |
| 970 | | 0 | 0 | 0 | 2+ | 0 | AT | GLI | | |
| 971 | Down | + | + | 2+ | 1−2+ | +− | AT | GLI | | |
| 972 | Down | + | + | + | + | − | AT | GLI | | |
| 973 | Up | − | − | − | − | + | AT | GLI | | |
| 974 | Up | + | + | 2+ | 3+ | 2+ | CA | Yale | | |
| 975 | | + | +− | 1−2+ | 2+ | ? | CA | Yale | GBM77693 | HUMAN DIAMINE ACETYLTRANSFERASE |
| 976 | | 1−2+ | 1−2+ | 2−3+ | 3+ | ? | CA | Yale | Z14136 | HOMO SAPIENS GENE SPERMIDINE/ SPERMINE N1-ACETYLTRANSFERASE |
| T132 | | | | | | | CA | | | |
| T133 | | | | | | | CA | | | |
| 977 | Up | + | + | 1−2+ | 2−3+ | 1−2+ | CA | Yale | | |
| T135 | | | | | | | CA | | | |
| 978 | Down | 2+ | 2+ | 2+ | 2+ | − | CA | GLI | G05563 | Human STS WI-7246 |
| 979 | Down | + | + | + | + | − | CA | GLI | | |
| 980 | | − | − | − | + | − | CA | GLI | | |
| 981 | Down | + | + | + | + | − | CA | GLI | 473168 | Human cosmid LUCA22 |

TABLE 1-continued

| Clones | mRNA Expression Pattern | Control | 10' | 30' | 60' | 120' | n1n2 | Sequenced by | Closest Genbank Acc. # | Closest Homology |
|---|---|---|---|---|---|---|---|---|---|---|
| 982 | | − | − | − | + | − | CA | GLI | M55542 | Human granulyte binding M55542 protien Isoform I |
| 983 | | − | − | − | + | − | CA | GLI | | |
| 984 | | 2+ | 2+ | 3+ | 3−4+ | 2+ | CC | Yale | HS167A14 | Z94721 HUMAN DNA SEQ-PAC167A 14 CHROM6 927 |
| T139 | Up | + | +− | + | − | 2+ | CC | GLI | | |
| 985 | Down | + | + | + | 2+ | +− | CC | Yale | | |
| T140 | Up | + | + | + | + | 2+ | CC | GLI | | |
| 986 | Down | 2+ | 2+ | 1−2+ | 1−2+ | +− | CC | Yale | AI015836 | 0V51H11.SI SOARES TESTIS NHT HOMO SAPIENS |
| 987 | | 2−3+ | 2+ | 2+ | 3−4+ | 3+ | CC | Yale | | |

TABLE 2

| Cln | Sequence |
|---|---|
| 846 | 1 TCTCAGTGAG CTGAGATCAC ACCACTGCAC TCCAACTGGG CGACAGAGCA (SEQ ID NO:11)<br>51 AG |
| 854 | 1 CACTTTCCCC AAATTCTTTT GCCATAGTTC ACTCTCTACT GATAAGGCCA (SEQ ID NO:12)<br>51 C |
| 855 | 1 GGGAAAGTGG TGGGGTGGTG AGGGTCAATG TGCAGAAAAT CGATGTAACT (SEQ ID NO:13)<br>51 TGTAATACAG TTGAGTCAAC TGTGTGTTCA CAACAACTCT GAGAGTTAAC<br>101 ACCATTTCTA |
| 856 | 1 ATCTAAATAT TTTTCATACC GAGTTATTAA GGAGTCAGTA GTCTGTGCTA (SEQ ID NO:14)<br>51 CAATGCTGCA AAAAGCATCA CGTGGAAGAA TGGGAACTAT GCGTACTTTA<br>101 TGAAGTGATG TATAACACAA TGAACTCTGT TTTACAACTA CAGTGCTGCA<br>151 TTCAATTATC TTCCAT |
| 859 | 1 AAGCTCTGTA TACAAAAGTT ATTTATTTAG ATGTTCGAGG CATGTCTCTC (SEQ ID NO:15)<br>51 CTCACCTGTA AACTAACTGT TTTATAACAG CTTGTATCAC ATGTGTGAAG<br>101 TTAATGAATG TAATACTCCA ACAAGCCATT CATCAGATTG GCCAACAGCT<br>151 AGGATACAGT TAAATAATGG CGACCAGGTT GACAAGTCAT AATTGCGGTT<br>201 TGGGGGACCG TAGTTGCACC TCACCTAGAC CAACGTACGC ATGGCACTCG<br>251 ACCCAGGCGA ACAAAATTAA T |
| 863 | 1 TTTCTCAAGA AGAGATAAGA ATGAAAAGTC ATAGAACACA TCATGGAGGA (SEQ ID NO:16)<br>51 CCTGGACACA AATGCAGACA AGCAGCTGAG CTTCGAGGAG TTCATCATGC<br>101 TGATGGCGAG GCTAACCTGG GCCTCCCACG AGAAGATGCA CGAGGGTGAC<br>151 GATGGCCCTG GCCACCACCA TAAGCCAGGC CTCGGGGAGG GCACCCCCTA<br>201 AGACCACAGT GGACAAGATC ACAGTGGCCA CGGACACGGC CACAGTCATG<br>251 GTGGCCACGG CCACAGCCAC TAATCAGGAG GCCAGGCCAC CCTGCCTCTA<br>301 CCCAACCAGG GCCCCGGGGC CTGTTATGTC AAACTGTCTT GGCTGTGGGG |
| 866 | 1 NGATCTTTCT AGGAGGGAGA CACTGGCCNC TCAAATCGTC CAGCGACCTT (SEQ ID NO:17)<br>51 CCTCATCCAC CCCATCCCTC CCCAGTTCAT TGCACTTTGA TTAGCAGCGG<br>101 AACAAGGAGT CAGACATTTT AAGATGGTGG CAGTAGAGGC TATGGACAGG<br>151 GCATGCCACG TGGGCTCATA TGGGGCTGGG AGTAGTTGTC TTTCCTGCCA<br>201 CTAACGTTGA GCCCCTGGAG GCACTGAAGT GCTTAGTGTA CTTGGAGTAT<br>251 TGGGGTCTGA CCCCAAACAC CTTCCAGCTC CTGTAACATA CTGGCCTGGA<br>301 CTGTTTTCTC TCGGCTCCCC ATGTGTCCTG GTTCCCGTTT CTCCACCTAG<br>351 ACTGTGAACC TCTCGAGGGC AGGGACCACA CCCTGTACTG TTCTGTGTCT<br>401 TTCACAGCTC CTCCCACAAT GCTGAATATA CAGCAGGTGC TCAATAAATG<br>451 ATTCT |
| 871 | 1 GCAAGTGTGT TGTGTTACAG TGTCACAACA CCGAG (SEQ ID NO:18) |

TABLE 2-continued

| Cln | Sequence |
|---|---|
| 872 | 1 GATCTCTCCC TACGCAAAAC GTATTGTAGT GAAAGGGTCT TCTTTACTAC (SEQ ID NO:19)<br>51 CTTAATAAAA CAGCTAGTGT G |
| 874 | 1 GATCTAAATA CAAAGGATAT ACAGTCTTGA ATCTAAAATA ATTTGCTAAC (SEQ ID NO:20)<br>51 TATTTTGATT CTTCAGAGAG AACTACTA |
| 876 | 1 GATCTAGTCC GGACATGCTG TGTATATTGT AACGTTAAAT GAAAAAGAA (SEQ ID NO:21)<br>51 CCCCCCTTTG TATTATAGTC ATGCGGTCTT ATGTATGATA AACAGTTG |
| 878 | 1 GATCTTTTGT AGTCACCTCT GTATCTTATG TCTGGTTGAG GGGTGCTTTT (SEQ ID NO:22)<br>51 ACTTGTCTGG CATTTGCATT CAATGATCTT TCAGTCATGT CAGTTAGACT<br>101 AAAAATTATT TCTG |
| 880 | 1 CCCAAGCCCC TTGGACACTG CAGCTCTTTT CAGTTTTGC TTACACACAA (SEQ ID NO:23)<br>51 TTCATTCTTT GCAGCTAATT AAGCCGAAGA AGCGTGGGAA TCAAGTTTGG<br>101 AACAGAGATT AAAAAAGTTC TT |
| 881 | 1 GCTCTGGAGG ACAATCCAGG AACTACATTA CCTGGACTGT ATGCTGGTCA (SEQ ID NO:24)<br>51 TTTCTACAGA CAGCATTCAG TATTTGAGTG TACGGTAACT GTCTGGGGTG<br>101 ATTCCTATAA GATCATTATA CTG |
| 882 | 1 GATCTTTCTC CTTGAATATC TTTCGATAAA CAACAAGGTG GTGTGATCTT (SEQ ID NO:25)<br>51 AATATATTTG AAAAAAACTT CATTCTCGTG AGTCATTTAA ATGTGTACAA<br>101 TGTACACACT GGTACTTAGA GTTTCTGTTT GATTCTTTTT TAATAAACTA<br>151 C |
| 883 | 1 TGTCACTCAT GCCCTGGGAC TGCTTCTCCA GCCAGGCGGG CGCCATACGT (SEQ ID NO:26)<br>51 CCCACACTAG TGAAGGTCAA TGTCTCAGAA CAACACCTCT AT |
| 884 | 1 GATCTGGCCT GTTCCTGCGT CTGCGGAGCA GGCCTTGTCT CCCAGCTATC (SEQ ID NO:27)<br>51 TATAACCTTA CCTAGAGTGT CGACTTGTGG GTTCCTGTTG CTGAGACTTC<br>101 CTGGATGGAG CCGCCCTCAC CGCCGGACCC GTAGCACTGC GCGGAACTGT<br>151 GTCCAATAAA GT |
| 885 | 1 GATCTGATTT GCTAGTTCTT CCTTGTAGAG TTATAAATGG AAAGATTACA (SEQ ID NO:28)<br>51 CTATCTGATT AATAGTTTCT TCATACTCTG CATATAATTT GTGGCTGCAG<br>101 AATATTGTAA TTTGTTGCAC ACTATGTAAC AAAACAACTG AAGATATGTT<br>151 TAATAAATAT TGTACT |
| 894 | 1 GATCTTTATG AGAGCAGTAT TTTCTGTGTT TTCTTTTAA TTTACAGCCT (SEQ ID NO:29)<br>51 TTCTTATTTT GATATTTTTT TAATGTTGTG GATGAATGCC AGCTTTCAGA<br>101 CAGAGCCCAC TTAGCTTGTC CACATGGATC TCAATGCCAA TCCTCCATTC<br>151 TTCCTCTCCA GATATTTTTG GGAGTGACAA ACATTCTCTC ATCCTACTTA<br>201 GCCTACCTAG ATTTCTCATG ACGAGTTAAT GCATGTCCGT GGTTGGGTGC<br>251 ACCTGTAGTT CTGTTTATTG GTCA |
| 895 | 1 GATCTAAGTT AGTCCAAAAG CTAAATGATT TAAAGTCAAG TTGTAATGCT (SEQ ID NO:30)<br>51 AGGCATAAGC ACTCTATAAT ACATTAAATT ATAGGCCGAG CAATTAGGGA<br>101 ATGTTTCTGA AACATTAAAC TTGTATTTAT GTCACTAAAA TTCTAACACA<br>151 AACTTAAAAA ATGTGTCTCA TACATATGCT GTACTAGGCT TCATCATGCA<br>201 TTTCTAAATT TGTGTATGAT TTGAATATAT GAAAGAATTT ATACACGAGT<br>251 GTTATTTAAA ATTATTAAAA ATAAATGTA |
| 896 | 1 GATCTTATAG GCCTGTCTCA TCAGGTTGGT GTCAGCCCAG CTAGGATTAG (SEQ ID NO:31)<br>51 GCAGAATTGG GTGGGGGCTG TAGTGCACTT TTGGCACAGC ATGTACCTGT<br>101 CTGACTAATT CTCTGTCTTT TCTTTCCTGT TGCAATTCAT GGGTCTTAGC<br>151 ATCTTCTGAA TGGTGTTTAG TAGGTCATCC TGTTGATTTC CTGCTAGGGA<br>201 GTAGCATACT CTGGCTCTGT ACCACTGGCC AAGGGACTTA AGGATAGATG<br>251 AAGGGCTGCA GTTTTGTTAA ATGGAACAAT ATGAAGAGA |
| T103 | 1 GATCTTTCTC CTTGAGTATC TTTCGATAAA CAACAAAGTG GTGTGATCTT (SEQ ID NO:32)<br>51 AATATATTTG AAAAAAACTT CATTCTCGTG AGTCATTTAA ATGTGTACAA<br>101 TGTACACACT GGTACTTAGA GTTTCTGTTT GATTCTTTTT TAATAAACTA<br>151 C |
| T104 | 1 GATCTCTGCT CATAGAATGC ATGGGGAGCC TTCCAGCTCA CTCTCCCTGA (SEQ ID NO:33)<br>51 GGACTGGCTT GACAGGGGCT ATGGGTTTGC TTTGG |
| T105 | 1 GATCTGCGCT TCCAGAGCGC AGCTATCGGT GCTTTGCAGG AGGCAAGTGA (SEQ ID NO:34)<br>51 GGCCTATCTG GTTGGCCTTT TTGAAGCACAC CAACCTGTGT GCTATCCATG<br>101 CCAAACGTGT AACAATTATG CCAAAAGACA TCCAGCTAGC ACGCCGCATA<br>151 CGTGGAGAAC GTGCTTAAGA ATCCACTATG ATGGGAAACA |
| T107 | 1 GATCTAAATG TGAACAGTTT ACTAATGCAC TACTGAAGTT TAAATCTGTG (SEQ ID NO:35)<br>51 GCACAATCAA TGTAAGCATG GGGTTTGTTT CTCTAAATTG ATTTGTAATC<br>101 TGAAATTACT GAACAACTCC TATTCCCATT TTTGCTAAAC TCAATTTCTG |

TABLE 2-continued

| Cln | Sequence |
|---|---|
| | 151 GTTTTGGTAT ATATCCATTC CAGCTTAATG CCTCTAATTT TAATGCCAAC<br>201 AAAATTGGTT GTAATCAAAT TTTAAAATAA TAATAATTTG GC |
| T76 | 1 GCCTTTTCGA TAGTTTCGGG TCAGGTAAAA ATGGCCTCCT GGCGTAAGCT (SEQ ID NO:36)<br>51 TTTCAAGGTT TTTTGGAGGC TTTTTGTAAA TTGTGATAGG AACTTTGGAC<br>101 CTTGAACTTA CGTATCATGT GGAGAAGAGC CAATTTAACA AACTAGGAAG<br>151 ATGAAAAGGG AAATTGTGGC CAAAACTTTG GGAAAAGGAG GTTCTTAAAA<br>201 TCAGTGTTTC CCCTTT |
| T8 | 1 GATCTATGCA CAAGAACCCC TTTACCCCAT GACCAACATC GCAGACACAT (SEQ ID NO:37)<br>51 GTGCTGGCCA CCTGCTGAGC CCCAAGTGGA ACGAGACAAG CAGCCCTTAG<br>101 CCCTTCCCCT CTGCAGCTTC CAGGCTGGCG TGCAGCATCA GCATCCCTAG<br>151 AAAGCCATGT GCAGCCACCA GTCCATTGGG CAGGCAGATG TTCCTAATAA<br>201 AGCT |
| T81 | 1 GATCTTTCCT CCTGGTTACT GTGAAGCCTG TTGGTTTGCT GCTGTCGTTT (SEQ ID NO:38)<br>51 TTGAGGAGGG CCCATGGGGG TAGGAGCAGT TGAACCTGGG AACAAACCTC<br>101 ACTTGAGCTG TGCCTAGACA ATGTGAATTC CTGTGTTGCT AACAGAAGTG<br>151 GCCTGTAAGC TCCTGTGCTC CGGAGGGAAG CATTTCCTGG TAGGCTTTGA<br>201 TTTTTCTGTG TGTTAAAGAA ATTCAATCTA CTCATGATGT GTTATGCATA<br>251 AAACATTTCT GGAACATGGA TTTGTGTTCA CCTTAAATGT GAAAATAAAT<br>301 CCTA |
| T82 | 1 ATCTTTCCTC CTGGTTACTG TGAAGCCTGT TGGTTTGCTG CTGTCGTTTT (SEQ ID NO:39)<br>51 TGAGGAGGGC CCATGGGGGT AGGAGCAGTT GAACCTGGGA CAAACCTCA<br>101 CTTGAGCTGT GCCTAGACAA TGTGAATTCC TGTGTTGCTA ACAGAAGTGG<br>151 CCTGTAAGCT CCTGTGCTCC GGAGGGAAGC ATTTCCTGGT AGGCTTTGAT<br>201 TTTTCTGTGT GTTAAAGAAA TTCAATCTAC TCATGATGTG TTATGCATAA<br>251 AACATTTCTG GAACATGGAT TTGTGTTCAC CTTAAATGTG AAAATAAATC<br>301 CTATTTTCTA TG |
| T85 | 1 GATCTTTGGC AGCGCCATTG GACTCTTTGG GGTCATCGTC GCAATTCTTC (SEQ ID NO:40)<br>51 ATACCTCCAG AGTGAAGATG GGTGACTAGA TGATATGTGT GGGTGGGGCC<br>101 GTGCCTCACT TTTATTTATT GCTGGTTTTC CTGGGACAGC TGGAGCTGTG<br>151 TCCCTTAACC TTTCAGAGGC TTGGTGTTCA GGGCCCTCCC TGCACTCCCC<br>201 TCTTGCTGCG TGTTGATTTG GAGGCACTGC AGTCCAGGCC GAGTCCTCAG<br>251 TGCGGGGAGC AGGCTGCTGC TGCTGACTCT GTGCAGCTGC GCACCTGTGT<br>301 CCCCCACCTC CACCCTCAAC CCATCTTCCT AGTGTTTGTG AAATAAACTT<br>351 GGTATA |
| T98 | 1 GATCTTCCAC GTCTCCATCT CAGTACACAA TCATTTAATA TTTCCCTGTC (SEQ ID NO:41)<br>51 TTACCCCTAT TCAAGCAACT AGAGGCCAGA AAATGGGCAA ATTATCACTA<br>101 ACAGGTCTTT GACTCAGGTT CCAGTAGTTC ATTCTAATGC CTAGATTCTT<br>151 TTGTGGTTGT TGCTGGCCCA ATGAGTCCCT AGTCACATCC CCTGCCAGAG<br>201 GGAGTTCTTC TTTTGTGAGA CACTGTAA ACGACACAAG AGAACAAGAA<br>251 TAAAA |
| 933 | 1 TTATATATTT TTCTTAAATA TGTTTTATTG TCTTCTCTAA GCAAAAGTT (SEQ ID NO:42)<br>51 CTTAATAAAC ATAGTATTTC TCTCTGCGTC CTATTTCATT AGTGAAGACA<br>101 TAGTTCACCT AAAATGGCAT CCTGCTCTGA ATCTAGACTT TTTAGAAATG<br>151 GCATATGTTT TTGATGATAT GTCAACATTC AAAATAGTCC TAATTAAATT<br>201 GTTGGTAAA TGTAATGTCA ACTCTTTATA AACTTAAATA TAAACAAGTA<br>251 ATTAACCACT CTAAGTAATA AAACACATTT CACCTGTGTT CTGAGTGTA |
| 967 | 1 ATGAATCCTT GCCACCTCCA CCTGCAGAAC TGTTATAAAT ATTACAACTT (SEQ ID NO:43)<br>51 GCTTTTTAGC TGATCTTCCA TCCTCAAATG ACTCTTTTTT CTTTATATGT<br>101 TAACATATAT AAAATGGCAA CTGATAGTCA ATTTTGATTT TTATTCAGGA<br>151 ACTATCTGAA ATCTGCTCAG AGCCTATGTG CATAGATGAA ACTTTTTTTT<br>201 AAAAAAAGTT ATTTAACAGT AATCTATTTA CTAATTATAG TACCTATCTT<br>251 TAAAGTATAG TACATTTTAC ATATGTAAAT GGTATGTTTC AATAATTTAA<br>301 GAACTCTGAA ACAATCTACA TATACTTATT ACCCAGTACA GTTTTTTTTC<br>351 CCCTGAAAAG CTGTGTATAA AATTATGGTG AATAAACTTT TATGTTTCCA<br>401 TTTCAAAGAC CAGGGTGGAG AGGAATAAGA GACTAAGTAT ATGCTTCAAG<br>451 TTTTAAATTA ATACCTCAGG TATTAAAATA AATATTCCAA GTTTGTGGGA<br>501 AATGGGGAGA TTAAAATG |
| 978 | 1 TTATGTGGCC TTAGGTAGCT GGTTGTACAT CTTTCCCTAA ATCGATCCAT (SEQ ID NO:44)<br>51 GTTACCACAT AGTAGTTTTA GTTTAGGATT CAGTAACAGT GAAGTGTTTA<br>101 CTATGTGCAA CGGTATTGAA GTTCTTATGA CCACAGATCA TCAGTACTGT<br>151 TGTCTCATGT AATGCTAAAA CTGAAATGGT CCGTGTTTGC ATTGTTAAAA<br>201 ATGATGTGTG AAATAGAATG AGTGCTATGG TGTTGAAAAC TGCAGTGTCC<br>251 GTTATGAGTG CCAAAAATCT GTCTTGAAGG CAGCTACACT TTGAAGTGGT<br>301 CTTTGAATAC TTTTAATAAA TTTATTTTGA TA |
| 981 | 1 TAGGTGAACC CTTATTCTGC AGGGTTCTCC CTCCCACCTT AAAGAAGTTC (SEQ ID NO:45)<br>51 CCCTTATGTG GGTTGCCTGG TGAATGGCCT TCCTTCCCGC CAGAGGGCTT<br>101 GTGAACAGAC CGGAGAGGAC AGTGGATTGT TTATACTCCA GTGTACATAG |

TABLE 2-continued

| Cln | Sequence |
|---|---|
| | 151 TGTAATGTAG CGTGTTTACA TGTGTAGCCT ATGTTGTGGT CCATCAGCCC<br>201 CTCACATTCC TAGGGGTTTG AGATGCTGTA CGTGGTATGT GACACCAAAG<br>251 CCACCTCTGT CATTTGTTGT GATGTCTTTT CTTGGCAAAA GCCTTGTGTA<br>301 TATTTGTATA TTACACATTT GTACAGAATT TTGGAAGATT TTCAGTCTAG<br>351 TTGCCAAATC TGGCTCCTTT ACAAAAG |
| 982 | 1 AGAATCTCTT ATGTTCTCAG AGGAAGGTGG AAGAAACCAG GGGCAGGAGT (SEQ ID NO:46)<br>51 AGGAATTGAG TGATAAACAA TTGGGCTAAT GAAGAAAACT TCTCTTATTG<br>101 TTCAGTTCAT CCAGATTATA ACTTCAATGG GACACTTTAG ACCATTAGAC<br>151 AATTGACACT GGATTAAACA AATTCACATA ATGCCAAATA CACAATGTAT<br>201 TTATAGCAAC GTATAATTTG CAAAGATGGA CTTTAAAAGA TGCTGTGTAA<br>251 CTAAACTGAA ATAATTCAAT TACTTATTAT TTAGAATGTT AAAGCTTATG<br>301 ATAGTCTTTT CTAATTCTTA ACACTCTATC TTGAAATCTT TCTGAGTTTC<br>351 CCCAGAAGAG AATATGGGAT TTTTTTTGAC ATTTTTGACT CATTTAATAA<br>401 TGCTCTTGTG TTTACCTAGT ATATGTGAGC TTTGTCTTAT GTGTCAAAAG<br>451 TCCTAGGAAA GTGGTTGATG TTTCTTATAG CAATTAAAAA TTATT |
| 905 | 1 ATCTCAGTGA GCTGAGATCA CACCACTGCA CTCCAACTGG GCGACAGAGC (SEQ ID NO:47)<br>51 AAGA |
| 910 | 1 GATCTGTAAT TCAGGTGTTT TCTGTACAGC CATACGTAGA TAATGAAGCC (SEQ ID NO:48)<br>51 AAAAGGCTTT TAATTACACC ATGGCCTAAA ATAAATTCAT CA |
| 915 | 1 TATTTTTCAG CTGAGTTATT AGGGAGTCAT TATTCTGTGG TACAATGCTG (SEQ ID NO:49)<br>51 CAAAAAGCAT CATGTGGAAG AATGGGAACT ATGCTTACAT TATGAAGTGA<br>101 TGTATAACAC AATGCAAATC TG |
| 916 | 1 GATCTTTTTT CATTAAAAAA TGTTCAATTA TCAGGCCGGG TGCAGTGGGG (SEQ ID NO:50)<br>51 CTCATGCCTG TAATCCCAAC ACTTTGGGAG GCCGATGCAG GCGGATCACT<br>101 AGGTCAGCAG ATCGAGACCA TCCTGGCTAA CACAGTGAAA CCT |
| 921 | 1 GATCTTTATT TTTAGCCATG CACTGTTGTG AGGAAAATTA CCTGTCTTGA (SEQ ID NO:51)<br>51 CTGCCATGTG TTCATCATCT TAAGTATTGT AAGCTGCTAT GTATGGATTT<br>101 AAACCGTAAT CATATCTTTT TCCTATCTAT CTGAGGCACT GGTGGAATAA<br>151 AGAACCTGTA TATTTTACTT TGTTGCAGAT AGTCTTGCCG CATCTTGGCA<br>201 AGTTGCAGAGA A |
| 927 | 1 GATCTTCGTG AAGACCTGAC TGGTAAGACC ATCACCCTCG AGGTGGAGCC (SEQ ID NO:52)<br>51 CAGTGACACC ATCGAGAATG TCAAGGCAAA GATCCAAGAT AAGGAAGGCA<br>101 TCCCTCCTGA TCAGCAGAGG TTGATCTTTG CTGGGAAACA GCTGGAAGAT<br>151 GGACGCACCC TGTCTGACTA CAACATCCAG AAAGAGTCCA CTCTGCACTT<br>201 GGTCCTGCGC TTGAGGGGGG GTGTCTAAGT TTCCCCTTTT AAGGTTTCAA<br>251 CAAATTTCAT TGCACTTTCC TTTCAATAAA GTTG |
| 928 | 1 GATCTTTCCT CCTGGTTACT GTGAAGCCTG TTGGTTTGCT GCTGTCGTTT (SEQ ID NO:53)<br>51 TFGAGGAGGG CCCATGGGGG TAGGAGCAGT TGAACCTGGG AACAAACCTC<br>101 ACTTGAGCTG TGCCTAGACA ATGTGAATTC CTGTGTTGCT AACAGAAGTG<br>151 GCCTGTAAGC TCCTGTGCTC CGGAGGGAAG CATTTCCTGG TAGGCTTTGA<br>201 TTTTTCTGTG TGTTAAAGAA ATTCAATCTA CTCATGATGT GTTATGCATA<br>251 AAACATTTCT GGAACATGGA TTTGTGTTCA CCTTAAATGT GAAAATAAAT |
| 930 | 1 GATCTTTCGG GTTCTCTCTC CTAACTCAGC TCTTCGTTCC CAGAAACCCA (SEQ ID NO:54)<br>51 GATGTAATCC CCCTACGTGG TGCTTGGGGC ATCCCGATAC CATCTCAGTA<br>101 AATCTCCTAC ATTGGCCTCC TCACCCTCCC CGGGACCCAC ACCCTTCAGG<br>151 TCCTCACCCT GAGACAGGAG GGACCCTCTG AGATCAGGGA CCCTTAGGTC<br>201 TCACTGCTCT CTGATTCATA GCTCAACTGG GCCCCCAGTT CCATACCCCA<br>251 GCATTCCCGG TCACTCCCTC CCTAATCTGA GCATCACTCA AGCTCTTTAT<br>301 TAAACTC |
| 939 | 1 ATCTCTCTCC CTACGCAAAA CCCTATTGTA GTAAAAAAGT CTTCTTTACT (SEQ ID NO:55)<br>51 ATCTTAATAA AACAGATATT GTG |
| 945 | 1 ATCTATTCTT GTAGATTTTT TTTGTGTGGG TCTATGTTTC ATTCATCTGC (SEQ ID NO:56)<br>51 TTTCAGGCTG GATTTATAAC AAGCAGAACT TTTAAACG |
| 949 | 1 GATCTAAATA TTTTTCAGCT GAGTTATTAC GGAGTCATTA TTCTGTGGTA (SEQ ID NO:57)<br>51 CAATGCTGCA AAAAGCATCA TGTGGAAGAA TGGGAACTAT GCTTACTTTA<br>101 TGAAGTGATG TATAACACAA TGAAA |
| 952 | 1 CTACCCCGTG ACTCAGTTAC CTCCCACTGG GTCCCTCCCA CATCATGTGG (SEQ ID NO:58)<br>51 GAATTGTAGG AGCTACAATT CAAGATGAGA TTTGGATGGG GTCACAGCCA<br>101 AACCTATCA CTGAGGTATC AAGGAGATTC TT |
| 954 | 1 GATCTGATTT GCTAGTTCTT CCTTGTAGAG TTATAAATGG AAAGATTACA (SEQ ID NO:59)<br>51 CTATCTGATT AATAGTTTCT TCATACTCTG CATATAATTT GTGGCTGCAG<br>101 AATATTGTAA TTTGTTGCAC ACTATGTAAC AAAACAACTG AAGATATGTT<br>151 TAATAAATAT TGTAGTTATT G |

TABLE 2-continued

| Cln | Sequence | | | | | |
|---|---|---|---|---|---|---|
| 975 | 1 NGATCTTTCT | CCTTGAATAT | CTTTCGATAA | ACAACAAGGT | GGTGTGATCT | (SEQ ID NO:60) |
| | 51 TAATATATTT | GAAAAAAACT | TCATTCTCGT | GAGTCATTTA | AATGTGTACA | |
| | 101 ATGTACACAC | TGGTACTTAG | AGTTTCTGTT | TGATTCTTTT | TTAATAAA | |
| 976 | 1 GATCTGCTAG | AAGATGGTTT | TGGAGAGCAC | CCCTTTTACC | ACTGCCTGGT | (SEQ ID NO:61) |
| | 51 TGCAGAAGTG | CCGAAAGAGC | ACTGGACTCC | GGAAGGTAAC | CCCTCGCCCT | |
| | 101 TTCCAGAAGC | CAGAGAGACC | AAGTGTTATG | TAAGAAGTAG | TGTCGGCTGT | |
| | 151 GTAGAACCAC | TGACTACACA | GGCCGAAGTT | ACTGAGAACT | TGGACAGAAA | |
| | 201 AAATAGCCAG | CAAGTGTT | | | | |
| 984 | 1 CATTCACACA | TTTAACCTCC | TTCCATACCA | AATCTT | | (SEQ ID NO:62) |
| 986 | 1 GATCTGGACA | GCAGAATGTT | ATAACGCAAG | TTCATGTGTT | GCTCCCAACT | (SEQ ID NO:63) |
| | 51 CCATTCTCTT | TTCTCTCGTG | CAACCAGTTT | GCCCATTCTC | TTCCTATTAC | |
| | 101 TTGCTC | | | | | |
| T113 | 1 TCAGAGATTT | GCAAAGACTC | ACGTTTTTGT | TGTTTTCTCA | TCATTCCATT | (SEQ ID NO:64) |
| | 51 GTGATACTAA | GAAACTAAGA | AGCTTAATGA | AAAGAAATAA | AATGCCTATG | |
| T116 | 1 GATCTGCGCT | TCCAGAGCGC | AGCTATCGGT | GCTTTGCAGG | AGGCAAGTGA | (SEQ ID NO:65) |
| | 51 GGCCTATCTG | GTTGGCCTTT | TTGAAGACAC | CAACCTGTGT | GCTATCCATG | |
| | 101 CCAAACGTGT | AACAATTATG | CCAAAAGACA | TCCAGCTAGC | ACGCCGCATA | |
| | 151 CGTGGAGAAC | GTGCTTAAGA | ATCCACTATG | ATGGGAAACA | | |
| T123 | 1 GATCTGTGAA | ATGCTATCTC | TCCTGAAGCA | ATACTGTTGA | CCAGAAAGGA | (SEQ ID NO:66) |
| | 51 CACTCCATAT | TGTGAAACCG | GCCTAATTTT | TCTGACTGAT | ATGGAAACGA | |
| | 101 TTGCCAACAC | ATACTTCTAC | TTTTAAATAA | ACAACTTTGA | TGATGTAACT | |
| | 151 TGACCTTCCA | GAGTTATGGA | AATTTTGTCC | CCATGTAATG | AATAAATTGT | |
| | 201 ATGTAT | | | | | |

EXAMPLE 4
Production of expression profiles generated from cDNAs made with RNA isolated from neutrophils isolated from a subject with a sterile inflammatory disease.

Neutrophils are isolated from normal donor peripheral blood following the LPS-free method or from subjects exhibiting the symptoms of a sterile inflammatory disease. RNA is extracted and the gene expression profiles prepared as described in Example 1.

To determine the identity of genes (cDNAs) which are differentially expressed in the neutrophils isolated from a subject exhibiting the symptoms of a sterile inflammatory disease, the cDNA profiles prepared from neutrophils from said subject are compared to profiles prepared from neutrophils isolated from the normal donor. Bands which exhibit altered intensities when compared between the gene expression profiles prepared from neutrophils from said subject and profiles prepared from neutrophils isolated from the normal donor are then extracted from the display gel as previously described in Example 1. The isolated fragments are then reamplified using 5' and 3' primers, subcloned into pCR-Script (Stratagene) and sequenced using an ABI automated sequencer.

Once sequences are obtained which correspond to the bands of interest, the sequences can be compared to known nucleic acid sequences in the available data bases.

EXAMPLE 5.
Method to identify a therapeutic or prophylactic agent that modulates the response of a granulocyte population to a pathogen The methods set forth in Example 1 offer a powerful approach for identifying therapeutic or prophylactic agents that modulate the expression of neutrophils or other granulocytic cells to a pathogen. For instance, profiles of normal granulocytes and neutrophils or other granulocytes exposed to pathogens such as E. coli, Y. pestis or other pathogenic bacteria are prepared as set forth in Example 1. A profile is also prepared from a granulocyte population that has been exposed to the pathogen in the presence of the agent to be tested. By examining for differences in the intensity of individual bands between the three profiles, agents which up or down regulate genes of interest in the pathogen exposed granulocytes can be identified.

As a specific example, screening for agents which up or down regulate the expression of human pre-B cell enhancing factor (PBEF) can be identified by examining the differences in band intensity between profiles produced from normal granulocytes, granulocytes exposed to the pathogen and granulocytes exposed to the pathogen in the presence of the agent to be tested. As shown in FIG. 4, PBEF is expressed at high levels when exposed to avirulent bacteria, including E. coli K12 and avirulent Y. pestis but is not expressed at high levels in granulocytes exposed to pathogenic Y. pestis. Agents that up regulate PBEF expression as demonstrated by increased band density in the profile produced from granulocytic cells exposed to virulent Y. pestis in the presence of the agent may be useful in modulating the response of neutrophils to bacterial infection.

EXAMPLE 6
Method to identify a therapeutic or prophylactic agent that modulates the expression of genes in a granulocyte cell population found in a subject having a sterile inflammatory disease.

The methods set forth in Example 4 offer a powerful approach for identifying therapeutic or prophylactic agents that modulate the expression of neutrophils or other granulocytic cells in subjects exhibiting the symptoms of a sterile (non-infectious) inflammatory disease. For instance, gene expression profiles of normal granulocytes and granulocytes from a subject exhibiting the symptoms of a sterile inflammatory disease are prepared as set forth in Examples 1 and 4. A profile is also prepared from a granulocyte population from a subject exhibiting the symptoms of a sterile inflammatory disease that have been exposed to the agent to be tested. By examining these profiles for differences in the intensity of band between the three profiles, agents which up or down regulate genes of interest in a granulocytic population from a subject exhibiting the symptoms of a sterile inflammatory disease can be identified. Agents that up-regulate a gene or genes that are expressed at abnormally low levels in a granulocytic cell population from a subject exhibiting the symptoms of a sterile inflammatory disease compared to a normal granulocytic cell population as well as agents that down regulate a gene or genes that are expressed at abnormally high levels in a granulocytic cell population from a subject exhibiting the symptoms of a sterile inflammatory disease are contemplated.

EXAMPLE 7

Production of solid support compositions comprising groupings of nucleic acids that correspond to the genes whose expression levels are modulated in a granulocytic population that has been exposed to a pathogen or nucleic acids that correspond to the genes whose expression levels are modulated in a granulocytic cell population from a subject having a sterile inflammatory disease.

As set forth in Examples 1–4, expression profiles from granulocytic cells exposed to a pathogen or granulocytic cells from a subject having a sterile inflammatory disease yield the identity of genes whose expression levels are modulated compared to normal, quiescent granulocytic cells.

Solid supports can be prepared that comprise immobilized representative groupings of nucleic acids corresponding to the genes or fragments of said genes from granulocytic cells whose expression levels are modulated in response to exposure to a pathogen or in a subject having a sterile inflammatory disease. For instance, representative nucleic acids can be immobilized to any solid support to which nucleic acids can be immobilized, such as positively charged nitrocellulose or nylon membranes (see Sambrook et al. (1989) *Molecular Cloning: a laboratory manual* 2nd., Cold Spring Harbor Laboratory) as well as porous glass wafers such as those disclosed by Beattie (WO 95/11755). Nucleic acids are immobilized to the solid support by well established techniques, including charge interactions as well as attachment of derivatized nucleic acids to silicon dioxide surfaces such as glass which bears a terminal epoxide moiety. A solid support comprising a representative grouping of nucleic acids can then be used in standard hybridization assays to detect the presence or quantity of one or more specific nucleic acid species in a sample (such as a total cellular mRNA sample or cDNA prepared from said mRNA) which hybridize to the nucleic acids attached to the solid support. Any hybridization methods, reactions, conditions and/or detection means can be used, such as those disclosed by Sambrook et al. (1989) *Molecular Cloning: a laboratory manual* 2nd., Cold Spring Harbor Laboratory, Ausbel et al.(1987) *Current Protocols in Molecular Biology*, Greene Publishing and Wiley-Interscience or Beattie (WO 95/11755).

One of ordinary skill in the art may determine the optimal number of genes that must be represented by nucleic acid fragments immobilized on the solid support to effectively differentiate between samples, e.g. neutrophils exposed to various pathogens or neutrophils isolated from a patient to be tested for a sterile inflammatory disease. Preferably, at least about 5, 10, 20, 50, 100, 150, 200, 300, 500, 1000 or more preferably, substantially all of the detectable mRNA species in a cell sample or population will be present in the gene expression profile or array affixed to a solid support. More preferably, such profiles or arrays will contain a sufficient representative number of mRNA species whose expression levels are modulated under the relevant infection, disease, screening, treatment or other experimental conditions. In most instances, a sufficient representative number of such mRNA species will be about 1, 2, 5, 10, 15, 20, 25, 30, 40, 50, 50–75 or 100 in number and will be represented by the nucleic acid molecules or fragments of nucleic acid molecules immobilized on the solid support. For example, nucleic acids encoding all or a fragment of one or more of the known genes or previously reported ESTs that are identified in FIG.4 and Tables 1 and 2 may be so immobilized. The skilled artisan will be able to optimize the number and particular nucleic acids for a given purpose, i.e., screening for modulating agents, identifying activated granulocytes, etc.

EXAMPLE 9.

Method of diagnosing exposure of a subject to a pathogen.

Expression profiles of RNA expression levels from neutrophils exposed to various bacteria, such as those disclosed in Examples 1 and 3, offer a powerful means to diagnose exposure of a subject to a pathogen. As set forth in Examples 1 and 3, the display patterns generated from cDNAs made with RNA isolated from neutrophils exposed to pathogenic and nonpathogenic *E. coli* and *Y. pestis* exhibit unique patterns of cDNA species corresponding to neutrophil mRNA species (genes) whose expression levels are modulated in response to contact of the neutrophils with the bacteria. The contacting of neutrophils with different species of pathogens may result in the production of expression profiles that are unique to each pathogen species or strain. These unique expression profiles are useful in diagnosing whether a subject has been exposed to or is infected with a given pathogen.

Briefly, expression profiles are produced as set forth in Example 1 using neutrophil samples exposed to various pathogens, such as pathogenic strains of *E. coli, Y. pestis*, Staphylococci, Streptococci or any other bacterial species. Neutrophils are then isolated from the subject to be tested for exposure to a pathogen and an expression profile prepared from the subject's neutrophils by the methods set forth in Example 1. The expression profile prepared from the subject neutrophils can then be compared to the expression profiles prepared from neutrophils exposed to the various pathogen species or strains to determine which expression profile most closely matches the expression profile prepared from the subject, thereby, diagnosing exposure of the subject to a pathogen.

EXAMPLE 10

Method of diagnosing a sterile inflammatory disease in a subject Expression profiles of RNA expression levels from neutrophils isolated from a subject having a sterile inflammatory disease, such as those disclosed in Example 4, offer a powerful means to diagnose inflammatory diseases such as psoriasis, rheumatoid arthritis, glomerulonephritis, asthma, cardiac and renal reperfusion injury, thrombosis, adult respiratory distress syndrome, inflammatory bowel diseases such as Crohn's disease and ulcerative colitis and periodontal disease. As set forth in Example 4, the gene expression profiles generated from cDNAs made with RNA isolated from neutrophils from subjects having various sterile inflammatory diseases may exhibit unique patterns of cDNA species corresponding to neutrophil mRNA species (genes) whose expression levels are modulated during the inflammatory process. These unique expression profiles are useful in diagnosing whether a subject has a sterile inflammatory disease.

Briefly, expression profiles are produced as set forth in Examples 1 and 4 using neutrophil samples isolated from patients with various sterile inflammatory diseases. Neutrophils are then isolated from the subject to be tested and an expression profile prepared from the subject's neutrophils by the methods set forth in Example 1. The expression profile prepared from the subject neutrophils can then be compared to the expression profiles prepared from neutrophils isolated from patients with various sterile inflammatory diseases to determine which expression profile most closely matches the expression profile prepared from the subject, thereby, diagnosing whether the subject as a sterile inflammatory disease.

It should be understood that the foregoing discussion and examples merely present a detailed description of certain preferred embodiments. It therefore should be apparent to those of ordinary skill in the art that various modifications and equivalents can be made without departing from the spirit and scope of the invention. All articles, patents and texts that are identified above are incorporated by reference in their entirety.

What is claimed is:

1. A method of diagnosing a sterile inflammatory disease in a patient comprising,
   (a) isolating a granulocyte population from the patient,
   (b) preparing a gene expression profile of said granulocyte population;
   (c) comparing the gene expression profile of step (b) to at least one gene expression profile of a granulocyte population from a subject known to have a sterile inflammatory disease or a gene expression profile of a granulocyte population from a subject that does not have a sterile inflammatory disease, to diagnose a sterile inflammatory disease in the patient.

2. The method of claim 1, wherein the sterile inflammatory disease is selected from the group consisting of glomerulonephritis, psoriasis, rheumatoid arthritis, asthma, cardiac and renal reperfusion injury, thrombosis, adult respiratory distress syndrome, periodontal disease and inflammatory bowel disease.

3. The method of claim 1, wherein the sterile inflammatory disease is glomerulonephritis.

4. The method of claim 1, wherein the granulocyte population is a neutrophil population, an eosinophil population, a basophil population, or a combined population of different granulocytic cells.

5. The method of claim 1, wherein the granulocyte population is a neutrophil population.

6. The method of claim 1, wherein the granulocyte population is from peripheral blood.

7. The method of claim 2, wherein the inflammatory bowel disease is Crohn's disease, of ulcerative colitis.

8. A method of diagnosing a sterile inflammatory disease in a patient comprising,
   (a) preparing a gene expression profile from isolated polymorphonuclear white blood cells from the patient;
   (b) comparing the gene expression profile of step (a) to at least one gene expression profile of polymorphonuclear white blood cells from a subject known to have a sterile inflammatory disease or a gene expression profile of polymorphonuclear white blood cells from a subject that does not have a sterile inflammatory disease, to diagnose a sterile inflammatory disease in the patient.

9. The method of claim 8, wherein the sterile inflammatory disease is selected from the group consisting of glomerulonephritis, psoriasis, rheumatorid arthritis, asthma, cardiac and renal reperfusion injury, thrombosis, adult respiratory distress syndrome, periodontal disease and inflammatory bowel disease.

10. The method of claim 8, wherein the inflammatory bowel disease is Crohn's disease or ulcerative colitis.

11. The method of claim 8, wherein the polymorphonuclear white blood cells are neutrophils, eosinophils, basophils, or a combination of different polymorphonuclear white blood cells.

12. The method of claim 8, wherein the polymorphonuclear white blood cells are neutrophils.

13. The method of claim 8, wherein the polymorphonuclear white blood cells are isolated from peripheral blood.

14. The method of claim 9, wherein the sterile inflammatory disease is glomerulonephritis.

15. A method of diagnosing glomerulonephritis in a patient comprising,
   (a) isolating polymorphonuclear white blood cells from the patient;
   (b) isolating RNA from the isolated polymorphonuclear white blood cells;
   (c) preparing a gene expression profile from the isolated RNA;
   (d) comparing the gene expression profile of step (c) to at least one gene expression profile of polymorphonuclear white blood cells from a subject known to have a sterile inflammatory disease or a gene expression profile of polymorphonuclear white blood cells from a subject that does not have a sterile inflammatory disease, to diagnose glomerulonephritis in the patient.

16. The method of claim 15, wherein the polymorphonuclear white blood cells are neutrophils, eosinophils, basophils, or a combination of different granulocytes.

17. The method of claim 15, wherein the polymorphonuclear white blood cells are neutrophils.

18. The method of claim 15, wherein the polymorphonuclear white blood cells are isolated from peripheral blood of the patient.

19. A method of any one of claims 1, 8, or 15, wherein the expression profile comprises the expression level of at least about 5 genes.

20. The method of claim 19, wherein the expression profile comprises the expression level of at least about 10 genes.

21. The method of claim 19, wherein the expression profile comprises the expression level of at least about 50 genes.

22. The method of claim 19, wherein the expression profile comprises the expression level of at least about 100 genes.

23. The method of claim 19, wherein the expression profile is prepared by hybridization of nucleic acids to nucleic acids immobilized on a solid substrate.

24. The method of claim 23, wherein the solid substrate is selected from the group consisting of nitrocellulose membrane, nylon membrane, silicon wafer, and borosilicate slide.

* * * * *